(12) United States Patent
Criscione et al.

(10) Patent No.: US 10,463,496 B2
(45) Date of Patent: *Nov. 5, 2019

(54) SELF-EXPANDING HEART ASSIST DEVICE

(71) Applicants: THE TEXAS A&M UNIVIERSITY SYSTEM, College Station, TX (US); Corinnova Incorporated, Houston, TX (US)

(72) Inventors: John C. Criscione, College Station, TX (US); Christina M. Bolch, Houston, TX (US); Boris Leschinsky, Mahwah, NJ (US)

(73) Assignees: The Texas A&M University System, College Station, TX (US); Corlnnova Incorporated, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/811,226

(22) Filed: Nov. 13, 2017

(65) Prior Publication Data

US 2018/0193147 A1 Jul. 12, 2018

Related U.S. Application Data

(63) Continuation-in-part of application No. 15/211,662, filed on Jul. 15, 2016, now Pat. No. 9,833,318.

(60) Provisional application No. 62/192,725, filed on Jul. 15, 2015.

(51) Int. Cl.
*A61F 2/24* (2006.01)
*A61M 1/10* (2006.01)
*A61M 1/12* (2006.01)

(52) U.S. Cl.
CPC .... *A61F 2/2481* (2013.01); *A61F 2002/2484* (2013.01)

(58) Field of Classification Search
CPC .............................................. A61F 2002/2484
See application file for complete search history.

*Primary Examiner* — Brian T Gedeon
(74) *Attorney, Agent, or Firm* — Chainey P. Singleton

(57) ABSTRACT

The present invention includes a device and method for a self-expanding framework device adapted to facilitate the deployment of an extra-cardiac device. The device includes a deployment tube and a self-expanding wire framework having a structure that results in the self-expanding wire framework circumferential flaring motion and bending outwardly to advance around the heart.

17 Claims, 19 Drawing Sheets

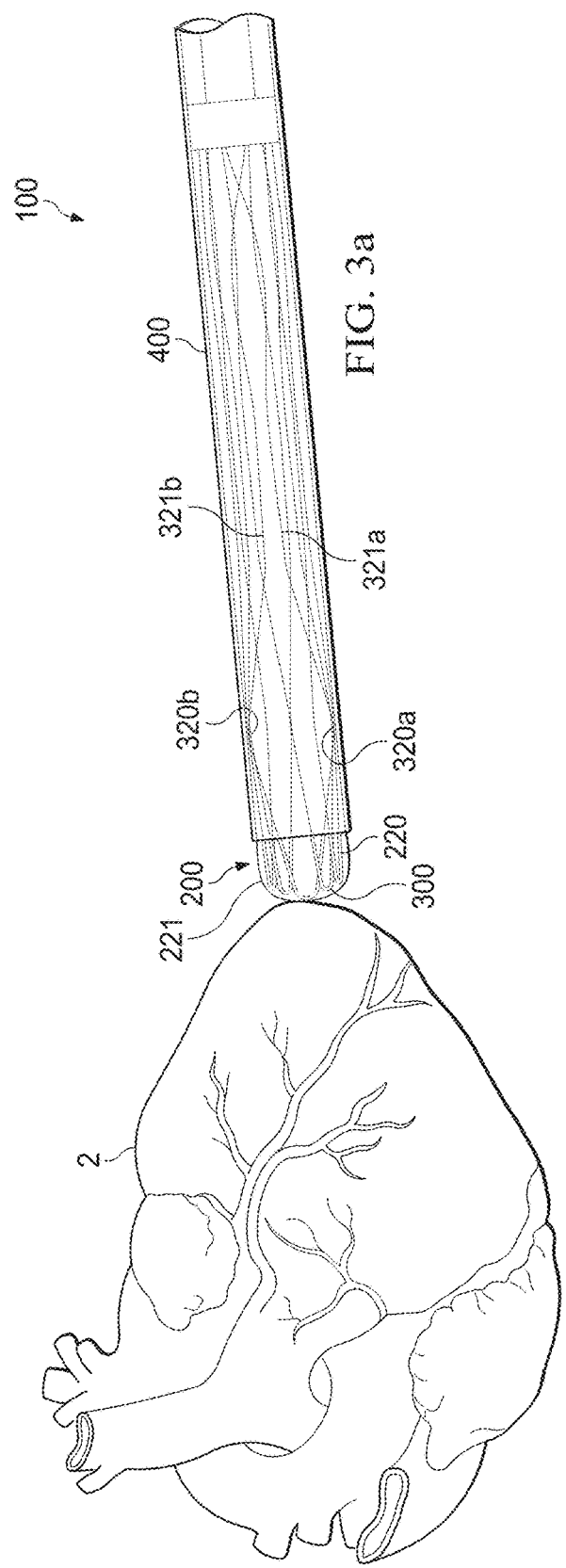

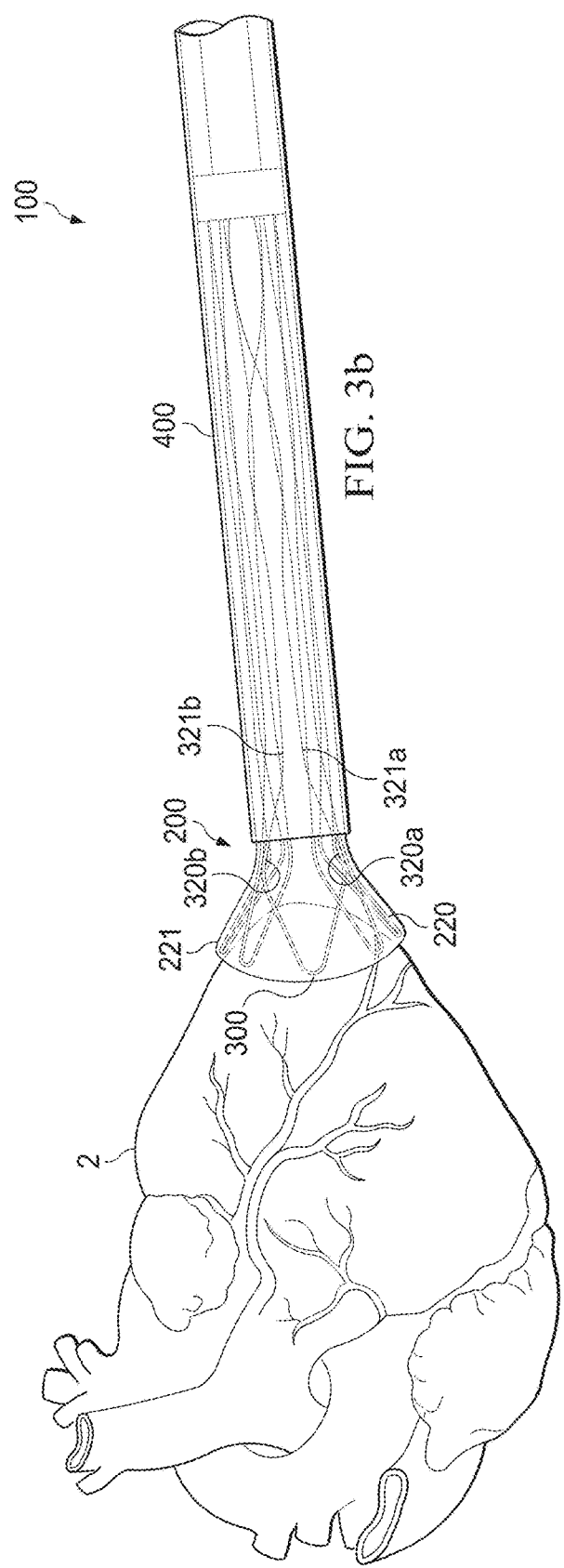

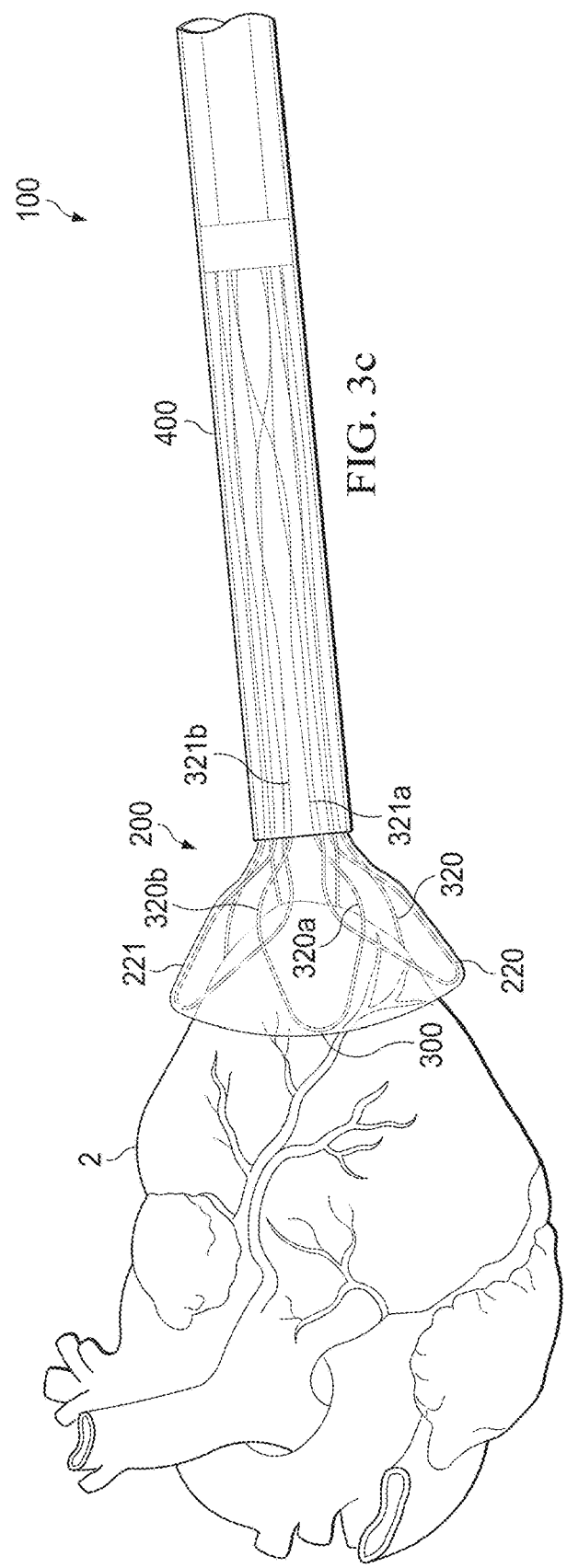

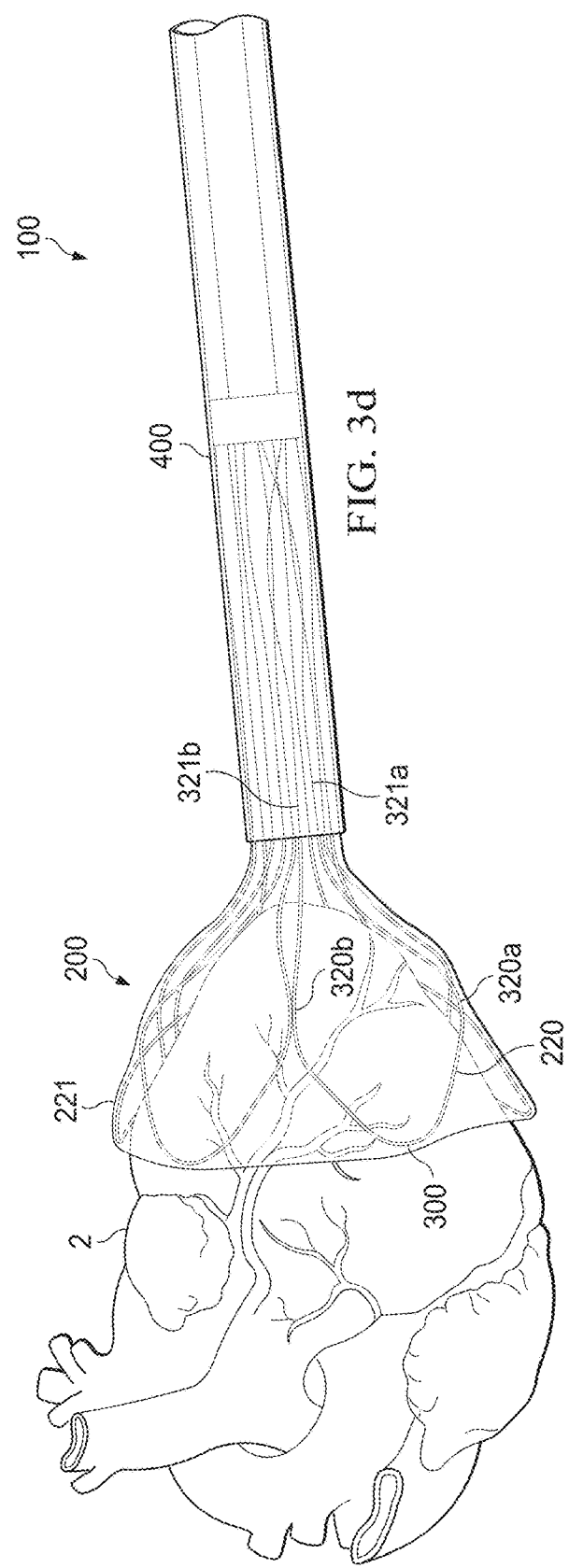

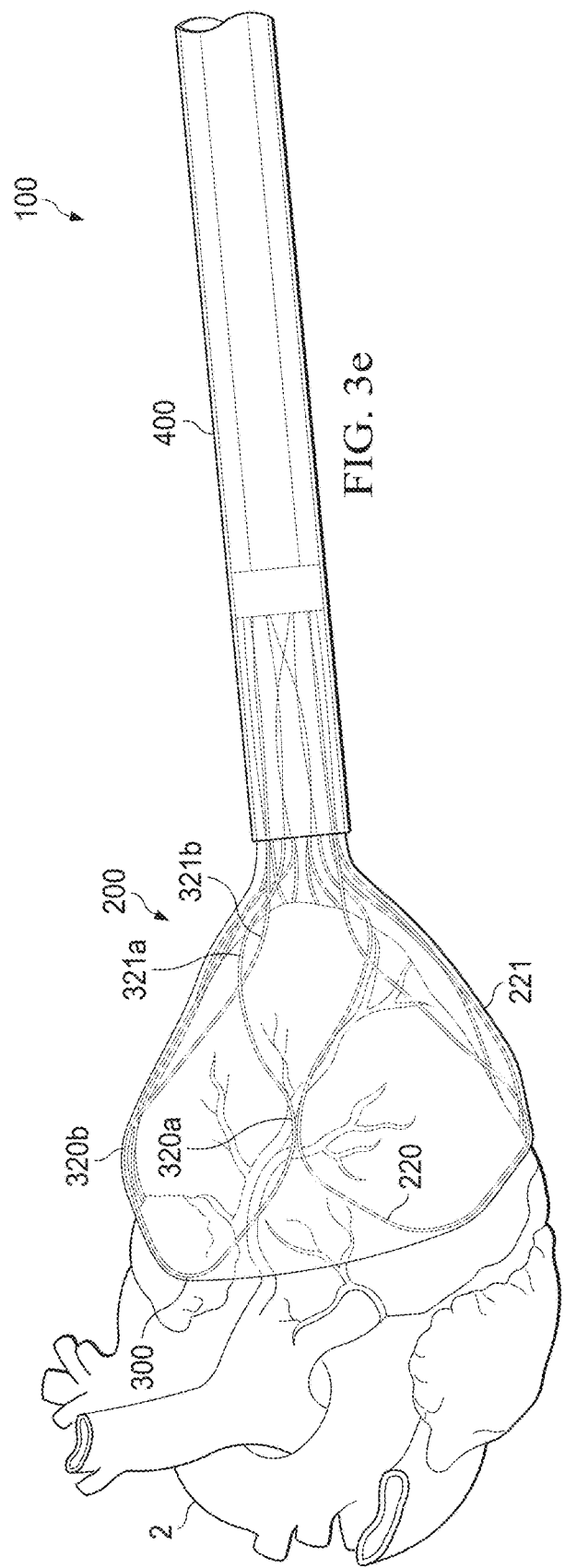

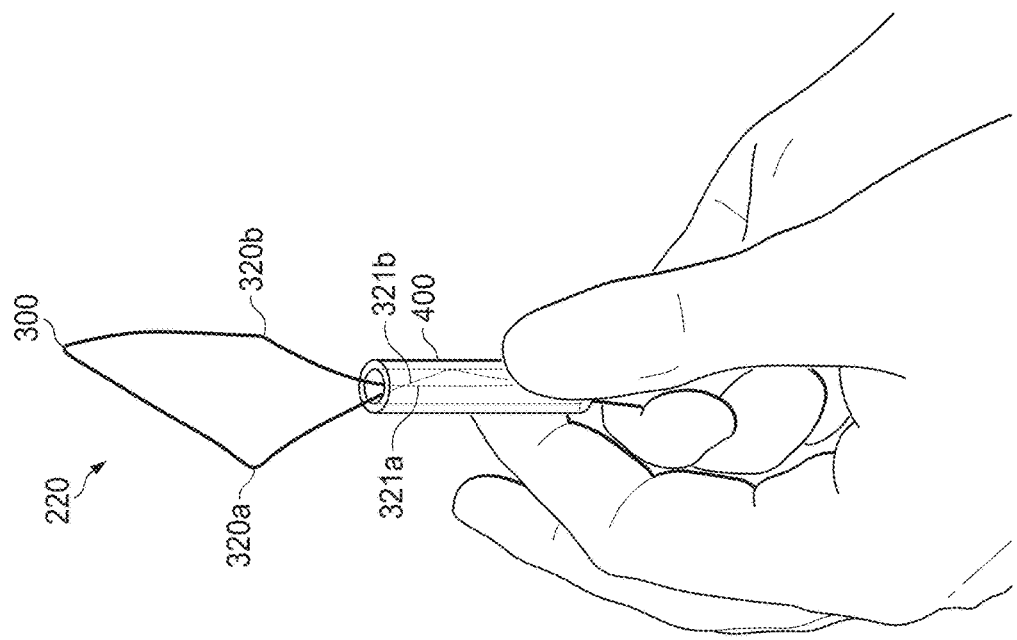
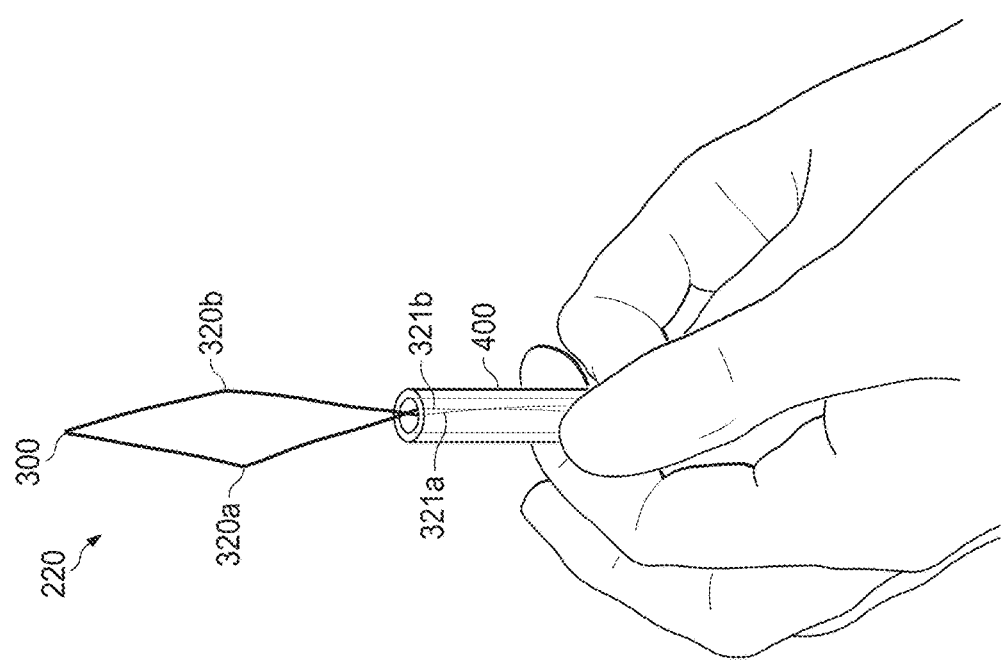

SELF-EXPANDING HEART ASSIST DEVICE

CROSS-REFERENCE TO RELATED APPLICATIONS

This application claims is a continuation of U.S. patent Application Ser. No. 62/192,725 filed Jul. 15, 2016 with claims priority to U.S. Provisional application Ser. No. 15/211,662 filed Jul. 15, 2015, the entire contents of each of which is incorporated herein by reference.

TECHNICAL FIELD OF THE INVENTION

The present invention relates in general to the field of heart assist devices, and more particularly, to a method and device for minimally invasive delivery of extra-cardiac devices.

STATEMENT OF FEDERALLY FUNDED RESEARCH

Not applicable.

INCORPORATION-BY-REFERENCE OF MATERIALS FILED ON COMPACT DISC

Not applicable.

BACKGROUND OF THE INVENTION

Without limiting the scope of the invention, its background is described in connection with methods and devices for delivery or deployment of minimally invasive extra-cardiac devices. One treatment for patients who suffer from either a myocardial infarction or CHF is the implantation of a direct cardiac compression device. Currently, a sternotomy is the preferred method of implantation of the cardiac compression device. Sternotomy is a type of surgical procedure in which a vertical inline incision is made along the sternum, after which the sternum itself is divided, or "cracked". This procedure provides access to the heart for surgical procedures. Conventional direct cardiac compression devices, such as the Anstadt cup, require a sternotomy for implantation, which is a very painful procedure. Disadvantageously, sternotomies result in long recovery times and a high risk of infection. Further, there is a high risk of complications due to the lengthy surgery required for these unstable patients.

Current approaches to minimally invasive implantation of heart-assist devices of various types suffer the shortcoming of being relatively slow and difficult procedures, resulting in additional stress on the patient and reducing the likelihood of a favorable outcome. Current minimally invasive devices may be deployed via a system of guidewires placed between the pericardium and the heart. There is a need to insert minimally invasive assistive biotechnology apparatuses such as a direct cardiac compression device (DCCD) in a minimally invasive way without the use of guidewires.

SUMMARY OF THE INVENTION

The present inventors recognized a need for minimally invasive devices to be deployed without the help of guidewires. In addition to speeding up insertion procedure, the present invention reduces the risk of guidewire entanglement to the patient.

The present invention provides a self-expanding wire framework comprising: a self-expanding wire framework covered with a polymer film adapted to flare outwardly to encircle a portion of the heart, wherein the self-expanding wire framework comprises: a set of articulated wire loops extending from a lead edge to a hub, wherein each of the articulated wire loops of the set of articulated wire loops comprise a top segment positioned at the lead edge and that extends to a left midway bend and to a right midway bend, a left strut that extends from the left midway bend to the hub, a right strut that extends from the right midway bend to the hub, and a fixed strut attachment point on the hub to fix the position of the left strut and the right strut, wherein the left midway bend and right midway bend result in a tension that causes the self-expanding wire framework and the polymer film to engage in a circumferential flaring motion and bend outwardly as the self-expanding framework is deployed from the deployment tube. The left midway bends and the right midway bends may be rounded to allow for gradual flaring as the self-expanding wire framework is deployed. The left midway bends and the right midway bends may be flattened to allow for flaring as the self-expanding wire framework is deployed. The left midway bends and the right midway bends may further comprise multiple bends to allow for immediate flaring positions as the self-expanding wire framework is deployed. The articulated wire loops may be a non-rounded wire. The set of articulated wire loops may comprises at least 2, 3, 4, 5, 6, 7, 8, 9, 10, 11, 12, 13, 14, 15, 16, 17, 18, 19, 20 or more articulated wire loops. The left strut may be connected to the right strut between the midway bend and the hub. The left strut may be intertwined with the right strut between the midway bend and the hub. The left strut and the right strut may be connected separately at the hub. Each of the articulated wire loops of the set of articulated wire loops may be positioned adjacent to an adjacent articulated wire loop. Each of the articulated wire loops of the set of articulated wire loops may be positioned to at least partially overlap the adjacent articulated wire loop. The polymer film may be on the inside of the self-expanding wire framework. The polymer film may be on the outside of the self-expanding wire framework. The polymer film may be on the inside and the outside to sandwich the self-expanding wire framework. The left strut and the right strut each may comprise a bend end connected to the midway bend and a hub end, wherein the hub end is secured to the hub at a fixed strut attachment point. The device may further comprising a deployment tube having an outer surface surrounding an inner passage and a deployment aperture at one end of the inner passage, wherein the self-expanding wire framework covered with a polymer film is slidably positioned in the inner passage to slidably extend from the deployment aperture and adapted to flare outwardly to encircle a larger portion of the heart. The self-expanding wire framework may be positioned inside the deployment tube and the top segments are bent, and the left midway bends and the right midway bends are straightened.

The present invention provides a self-expanding framework device adapted to facilitate the deployment of an extra-cardiac device, comprising: a deployment tube having an outer surface surrounding an inner passage and a deployment aperture at one end of the inner passage, and a self-expanding wire framework covered with a polymer film and slidably positioned in the inner passage to slidably extend from the deployment aperture and adapted to flare outwardly to encircle a larger portion of the heart, wherein the self-expanding wire framework comprises: a set of articulated wire loops extending from a lead edge to a hub, wherein each of the articulated wire loops of the set of articulated wire loops comprise a top segment positioned at the lead edge and that extends to a left midway bend and to a right midway bend, a left strut that extends from the left midway bend to the hub, a right strut that extends from the right midway bend to the hub, and a fixed strut attachment point on the hub to fix the position of the left strut and the right strut, wherein the left midway bend and right midway bend result in a tension that causes the self-expanding wire framework and the polymer film to engage in a circumferential flaring motion and bend outwardly as the self-expanding framework is deployed from the deployment tube.

The self-expanding wire framework is positioned inside the deployment tube with the top segments bent such that the left midway bends and the right midway bends are relatively straightened. The left midway bends and the right midway bends are rounded to allow for gradual flaring as the self-expanding wire framework is deployed from the deployment tube. The left midway bends and the right midway bends are flattened to allow for flaring as the self-expanding wire framework is deployed from the deployment tube. The left midway bends and the right midway bends further comprise multiple bends to allow for immediate flaring positions as the self-expanding wire framework is deployed from the deployment tube. The articulated wire loops may be a non-rounded wire. The set of articulated wire loops may comprises at least 2, 3, 4, 5, 6, 7, 8, 9, 10, 11, 12, 13, 14, 15, 16, 17, 18, 19, 20 or more articulated wire loops. The left strut may be connected to the right strut between the midway bend and the hub. The left strut may be intertwined with the right strut between the midway bend and the hub. The left strut and the right strut may be connected separately at the hub. Each of the articulated wire loops of the set of articulated wire loops may be positioned adjacent to an adjacent articulated wire loop. Each of the articulated wire loops of the set of articulated wire loops may be positioned to at least partially overlap the adjacent articulated wire loop. The polymer film may be on the inside of the self-expanding wire framework. The polymer film may be on the outside of the self-expanding wire framework. The polymer film may be on the inside and the outside to sandwich the self-expanding wire framework. The left strut and the right strut each may comprise a bend end connected to the midway bend and a hub end, wherein the hub end is secured to the hub at a fixed strut attachment point. The device may further comprising a deployment tube having an outer surface surrounding an inner passage and a deployment aperture at one end of the inner passage, wherein the self-expanding wire framework covered with a polymer film is slidably positioned in the inner passage to slidably extend from the deployment aperture and adapted to flare outwardly to encircle a larger portion of the heart. The self-expanding wire framework may be positioned inside the deployment tube and the top segments are bent, and the left midway bends and the right midway bends are straightened.

The present invention provides a method for implanting an extra-cardiac device about the heart using a self-expanding framework delivery device about a heart, comprising the steps of: providing a self-expanding framework delivery device comprising a deployment tube having an outer surface surrounding an inner passage and a deployment aperture at one end of the inner passage, and a self-expanding wire framework covered with a polymer film and slidably positioned in the inner passage to slidably extend from the deployment aperture and adapted to flare outwardly to encircle a larger portion of the heart, wherein the self-expanding wire framework comprises: a set of articulated wire loops extending from a lead edge to a hub, wherein each of the articulated wire loops of the set of articulated wire loops comprise a top segment positioned at the lead edge and that extends to a left midway bend and to a right midway bend, a left strut that extends from the left midway bend to the hub, a right strut that extends from the right midway bend to the hub, and a fixed strut attachment point on the hub to fix the position of the left strut and the right strut, wherein the left midway bend and right midway bend result in a tension that causes the self-expanding wire framework and the polymer film to engage in a circumferential flaring motion and bend outwardly as the self-expanding framework is deployed from the deployment tube; inserting the deployment tube into the thoracic cavity; deploying the self-expanding wire framework covered with a polymer film from the deployment aperture; bending outwardly of the self-expanding framework at the left midway bend and right midway to circumferential flare the lead edge of the articulated wire loops about the apex of the heart; and extending the self-expanding wire framework from the deployment aperture to encircle a portion of the heart. The left midway bends and the right midway bends may be rounded to allow for gradual flaring as the self-expanding wire framework is deployed. The left midway bends and the right midway bends may be flattened to allow for flaring as the self-expanding wire framework is deployed. The left midway bends and the right midway bends may further comprise multiple bends to allow for immediate flaring positions as the self-expanding wire framework is deployed. The articulated wire loops may be a non-rounded wire. The set of articulated wire loops may comprises at least 2, 3, 4, 5, 6, 7, 8, 9, 10, 11, 12, 13, 14, 15, 16, 17, 18, 19, 20 or more articulated wire loops. The left strut may be connected to the right strut between the midway bend and the hub. The left strut may be intertwined with the right strut between the midway bend and the hub. The left strut and the right strut may be connected separately at the hub. Each of the articulated wire loops of the set of articulated wire loops may be positioned adjacent to an adjacent articulated wire loop. Each of the articulated wire loops of the set of articulated wire loops may be positioned to at least partially overlap the adjacent articulated wire loop. The polymer film may be on the inside of the self-expanding wire framework. The polymer film may be on the outside of the self-expanding wire framework. The polymer film may be on the inside and the outside to sandwich the self-expanding wire framework. The left strut and the right strut each may comprise a bend end connected to the midway bend and a hub end, wherein the hub end is secured to the hub at a fixed strut attachment point. The device may further comprise a deployment tube having an outer surface surrounding an inner passage and a deployment aperture at one end of the inner passage, wherein the self-expanding wire framework covered with a polymer film is slidably positioned in the inner passage to slidably extend from the deployment aperture and adapted to flare outwardly to encircle a larger portion of the heart. The self-expanding wire framework may be positioned inside the deployment tube and the top segments are bent, and the left midway bends and the right midway bends are straightened.

The present invention provides a self-expanding wire framework comprising: a self-expanding wire framework covered with a polymer film. The polymer film may be a passive covering for the purposes of a passive device for diastolic heart failure. The passive covering may include one or more fluid chambers that are passively filled with fluid to compress the heart. The passive covering may include a port to adjust the volume of fluid in the passive chambers as desired.

In another embodiment the polymer film may include active inflation chambers to assist the heart. The device comprising a polymer film adapted to fit about the heart, wherein the polymer film is in contact with the heart; an outer film in contact with the biocompatible inner film; one or more fluid chambers formed between the biocompatible inner film and the outer film; and a fluid connection in fluid communication with the one or more fluid chambers, wherein a fluid enters the one or more fluid chambers through the fluid connection to selectively compress the heart during a heart contraction and during recoil the fluid exits the one or more fluid chambers through the fluid connection to allow the heart to decompress. The device may further comprise a pneumatic driver operably linked to the fluid connection to pressurize the biocompatible inner membrane to compress the heart and depressurize the biocompatible inner membrane to aid in filling the heart. In another embodiment the polymer film comprises a biocompatible inner film pneumatically locked to the heart to allow the inner film to pull open the heart and aid in filling of the heart.

In another embodiment the polymer film may include both an active set of chambers and a passive set of chambers. The device comprising an inner polymer film comprising one or more passive chambers adapted to fit about the heart. Each of the one or more passive chambers may be individually filled with a fixed volume of fluid. This fixed volume of fluid may be varied through a port to change the size of the one or more passive chambers and thus the fitment of the device about the heart. The device also includes an outer film in contact with the inner film; one or more fluid chambers formed between the inner film and the outer film; and a fluid connection in fluid communication with the one or more fluid chambers, wherein a fluid enters the one or more fluid chambers through the fluid connection to selectively compress the heart during a heart contraction and during recoil the fluid exits the one or more fluid chambers through the fluid connection to allow the heart to decompress. The device may further comprise a pneumatic driver operably linked to the fluid connection to pressurize the biocompatible inner membrane to compress the heart and depressurize the biocompatible inner membrane to aid in filling the heart. In another embodiment the polymer film comprises a biocompatible inner film pneumatically locked to the heart to allow the inner film to expand the heart and aid in filling of the heart.

The present invention provides a self-expanding wire framework comprising: a self-expanding wire framework covered with a polymer film adapted to flare outwardly to encircle a portion of the heart, wherein the self-expanding wire framework comprises: a set of articulated wire loops extending from a lead edge to a hub, wherein each of the articulated wire loops of the set of articulated wire loops comprise a top segment positioned at the lead edge and that extends to a left midway bend and to a right midway bend, a left strut that extends from the left midway bend to the hub, a right strut that extends from the right midway bend to the hub, and a fixed strut attachment point on the hub to fix the position of the left strut and the right strut, wherein the left midway bend and right midway bend result in a tension that causes the self-expanding wire framework and the polymer film to engage in a circumferential flaring motion and bend outwardly as the self-expanding framework is deployed from the deployment tube. The left midway bends and the right midway bends may be rounded to allow for gradual flaring as the self-expanding wire framework is deployed. The left midway bends and the right midway bends may be flattened to allow for flaring as the self-expanding wire framework is deployed. The left midway bends and the right midway bends may further comprise multiple bends to allow for immediate flaring positions as the self-expanding wire framework is deployed. The articulated wire loops may be a non-rounded wire. The set of articulated wire loops may comprises at least 2, 3, 4, 5, 6, 7, 8, 9, 10, 11, 12, 13, 14, 15, 16, 17, 18, 19, 20 or more articulated wire loops. The left strut may be connected to the right strut between the midway bend and the hub. The left strut may be intertwined with the right strut between the midway bend and the hub. The left strut and the right strut may be connected separately at the hub. Each of the articulated wire loops of the set of articulated wire loops may be positioned adjacent to an adjacent articulated wire loop. Each of the articulated wire loops of the set of articulated wire loops may be positioned to at least partially overlap the adjacent articulated wire loop. The polymer film may be on the inside of the self-expanding wire framework. The polymer film may be on the outside of the self-expanding wire framework. The polymer film may be on the inside and the outside to sandwich the self-expanding wire framework. The left strut and the right strut each may comprise a bend end connected to the midway bend and a hub end, wherein the hub end is secured to the hub at a fixed strut attachment point. The device may further comprising a deployment tube having an outer surface surrounding an inner passage and a deployment aperture at one end of the inner passage, wherein the self-expanding wire framework covered with a polymer film is slidably positioned in the inner passage to slidably extend from the deployment aperture and adapted to flare outwardly to encircle a larger portion of the heart. The self-expanding wire framework may be positioned inside the deployment tube and the top segments are bent, and the left midway bends and the right midway bends are straightened.

BRIEF DESCRIPTION OF THE DRAWINGS

For a more complete understanding of the features and advantages of the present invention, reference is now made to the detailed description of the invention along with the accompanying figures and in which:

FIGS. 3a-3e depicts the present invention at successive amounts of deployment about a plastic mock heart.

FIGS. 4a-4d depicts a side view of an embodiment of the present invention showing a single articulated wire loop being drawn into the deployment tube.

DETAILED DESCRIPTION OF THE INVENTION

Figure 1:
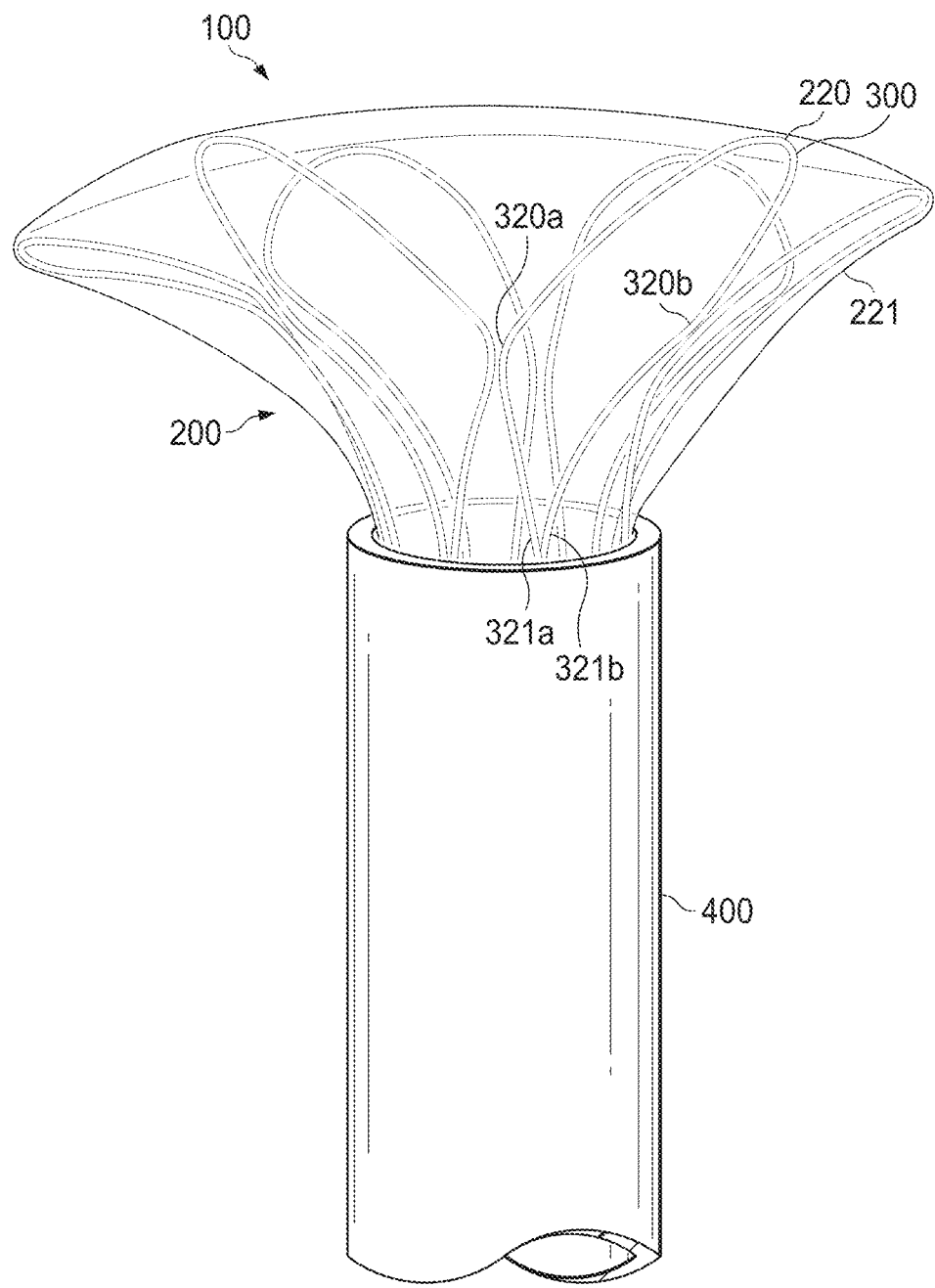
FIG. 1 depicts a frontal view of an embodiment of the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Though different devices exist today with specific indications for medium/long term support, devices that provide direct cardiac compression and aortic compression represent a significant innovation in the cardiac device industry as it can address both systolic and diastolic heart failure with a single device design.

The present invention is directed to a minimally invasive implantation apparatus and method and is adapted to save the lives of CHF patients and dramatically shorten their hospital stays. With the present invention, in combination with drug therapy and an exercise program, many of the patients receiving a deployed device, such as a cardiac compression device, in accordance with the present invention, could have restored cardiac function in as little as three weeks, allowing a shorter hospital stay and increased quality of life.

As noted, direct cardiac compression devices require a sternotomy for implantation. In contrast, the present invention permits at least a deployable device to be implanted quickly using a minimally invasive incision without the need for any assisting devices or guidewires. This allows patients to recover within a shorter period, resulting in a shorter hospital stays and less of a chance for infection.

As used herein the term "polymer" or "polymer film" is use to denote a polymeric composition that is biocompatible. Non-limiting examples of suitable, biocompatible, biostable, implantable materials include but are not limited to polyetherurethane, polycarbonateurethane, silicone, polysiloxaneurethane, hydrogenated polystyrene-butadiene copolymer, ethylene-propylene and dicyclopentadiene terpolymer, and/or hydrogenated poly(styrene-butadiene) copolymer, poly(tetramethylene-ether glycol) urethanes, poly(hexamethylenecarbonate-ethylenecarbonate glycol) urethanes elastomeric polyurethane, latex, polyetherurethane, polycarbonateurethane, silicone, polysiloxaneurethane, hydrogenated polystyrene-butadiene copolymer, ethylene-propylene and dicyclopentadiene terpolymer, hydrogenated poly(styrene-butadiene) copolymer, poly(tetramethylene-ether glycol) urethanes, poly(hexamethylenecarbonate-ethylenecarbonate glycol) urethanes and combinations thereof. In addition, the present invention may be reinforced with filaments, made of a biocompatible, biostable, implantable polyamide, polyimide, polyester, polypropylene, polyurethane etc. In addition, the device may be made from different materials in different regions of the device.

The present invention can be broadly viewed as a device comprising a deployment tube having an inner surface and an outer surface, and a self-expanding wire framework slidable along the inner surface. As shown in FIG. 1, embodiment 100 of the present invention comprises a deployment tube 400 with the self-expanding wire framework 200 having polymer film 221 and being partially deployed from the deployment tube 400. In one embodiment, the DCCD device (not shown) can be attached to the self-expanding wire framework 100 before being drawn into the deployment tube 400.

FIG. 1 shows the device 100 having a framework 200 with the polymer film 221 in contact six articulated wire loops 220 being deployed from tube 400. The leading edge or top segments 300 forms a framework 200 encloses the deployed device 100 around the heart (not shown). The self-expanding wire framework 200 comprises multiple articulated wire loops 220 adjacent each other but not intertwined and disposed in a polymer film 221. Each of the articulated wire loops 220 includes the midway bends 320*a* and 320*b* to create tension when the midway bends 320*a* and 320*b* rotate and straighten. The articulated wire loops 220 include strut 321*a* extending from midway bends 320*a* and strut 321*b* extending from midway bends 320*b*. In FIG. 1, the top segment 300 is pointed outwards or flaring, by doing so, the left and right midway bends 320*a* and 320*b*. When the top segment 300 is further deployed axially, the left and right midway bends 320*a* and 320*b* must become straighter or unbend forming a configuration with higher elastic energy. As left and right midway bends 320*a* and 320*b* of each further rotate and straighten out, this will orient the top segment 300 to straighten out from the initial flaring motion when the framework is first deployed.

Figure 2A:
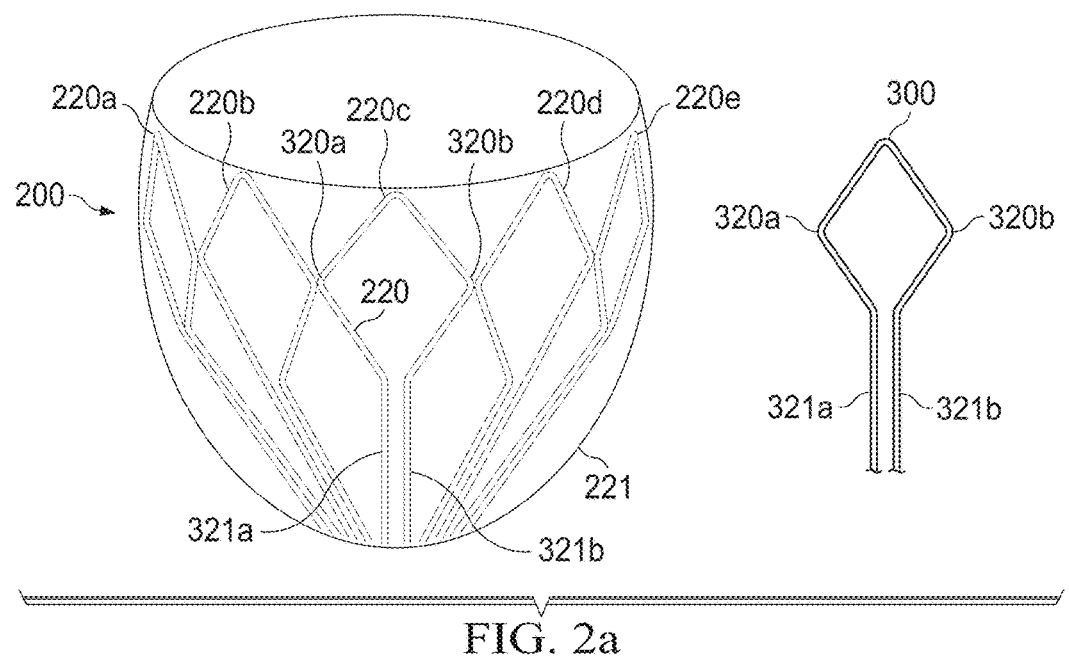
FIGS. 2a and 2b depict a schematic diagram of the elements of the self-expanding wire framework.
Figure 2B:
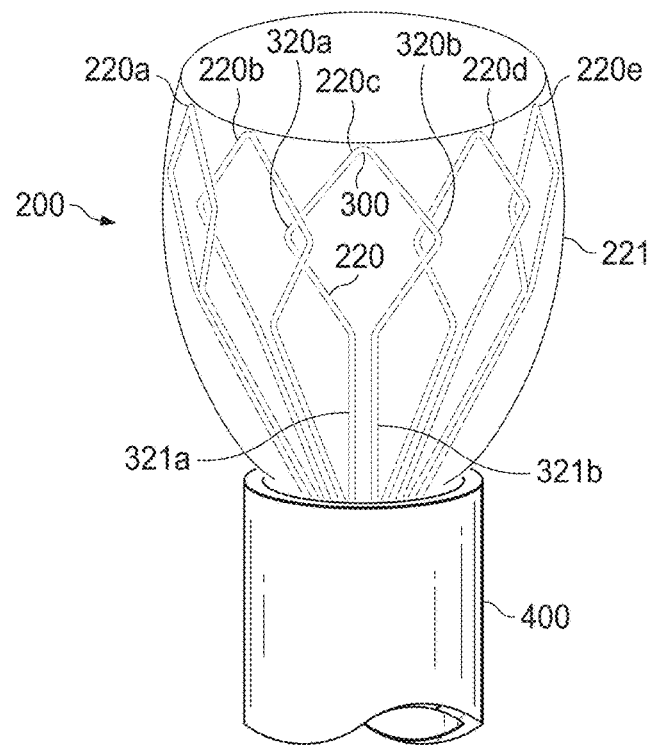

FIGS. 2*a* and 2*b* depict a schematic diagram of the elements of self-expanding wire framework 200 with a polymer film 221 covering. The self-expanding wire framework 200 is comprised of multiple articulate wire loops 220*a-e*, each comprising of a left and a right midway bends 320*a* and 320*b* that extend as struts 321*a* and 321*b* to hub (not shown). When the self-expanding wire framework 200 is being drawn into or compressed to fit inside the deployment tube (not shown), the top segment 300 of each articulated loops 220 is bent and compressed together to fit inside the deployment tube (not shown). The midway bends 320*a* and 320*b* of each articulated loop are straightened and compressed closer together to one another. The unbending or straightening of midway bends 320*a* and 320*b* is unstable causing it to twist or rotate rather than becoming a straight line (when struts 321*a* and 321*b* are not fixed relative to each other). When the left and right midway bends 320a and 320b of each articulated loop 220 are compressed closer together, the left and right midway bends 320a and 320b rotate and orient the top segment 300 out-of-plane creating a flaring motion. The unstable tendency of unbending makes the top segment 300 of each articulate loop 220 protrudes radially outwards away from the hoop dimension as the top segment 300 is partially deployed.

FIG. 2a shows a schematic diagram and the overall shape of the self-expanding wire framework 200 having adjacent articulated wire loops 220a-e and polymer film 221 fully deployed from the deployment tube (not shown). The leading edge or top segment 300 forms a circular framework 200 that encloses the deployed device around the heart (not shown). The self-expanding wire frame 200 comprises multiple articulated wire loops 220a-e disposed in a polymer film 221. The articulated wire loops 220a-e are adjacent each other but not intertwined. The polymer film 221 may be on one side (inner surface or outer surface) of the multiple articulated wire loops 220. The polymer film 221 may be on both sides (inner surface and outer surface) of the multiple articulated wire loops 220a-e forming a sandwich configuration. Alternatively, the polymer film 221 may be a single film with the multiple articulated wire loops 220a-e disposed within the polymer film 221. Each of the articulated wire loops 220a-e includes the midway bends 320a and 320b as shown in the diagram to create tension when the midway bends 320a and 320b rotate and straighten. The articulated wire loops 220a-e include strut 321a extending from midway bends 320a and strut 321b extending from midway bends 320b. The position of strut 321a and 321b are fixed relative each other so that the strut 321a and 321b themselves cannot rotate or turn thus forcing movement about the midway bends 320a and 320b. The left midway bend 320a and right midway bend 320b of each of the articulated wire loops 220a-e results in a tension that causes the self-expanding wire framework 200 to engage in a circumferential flaring motion and end out of plane when deployed from the deployment tube (not shown). Further deployment of the framework 200 allows the left and right midway bends 320a and 320b of each of the articulated wire loops 220a-e making up the framework 200 to straighten out in a configuration with higher elastic energy which reorients the top segment 300 back towards the center.

FIG. 2b shows a schematic diagram and the overall shape of the self-expanding wire framework 200 having overlapping articulated wire loops 220 with the polymer film 221 covering that is fully deployed from the deployment tube (not shown). The leading edge or top segment 300 forms a circular framework 200 that encloses the deployed device around the heart (not shown). The self-expanding wire framework 200 comprises multiple articulated wire loops 220 disposed in a polymer film 221 in a partially overlapping pattern with the adjacent wire loops 220 partially overlapping (but not intertwined). The polymer film 221 may be on one side (inner surface or outer surface) of the multiple articulated wire loops 220. The polymer film 221 may be on both sides (inner surface and outer surface) of the multiple articulated wire loops 220 forming a sandwich configuration. Alternatively, the polymer film 221 may be a single film with the multiple articulated wire loops 220 disposed with in the polymer film 221. Each of the articulated wire loops 220 includes the midway bends 320a and 320b as shown in the diagram to create tension when the midway bends 320a and 320b rotate and straighten. The articulated wire loops include strut 321a extending from midway bends 320a and strut 321b extending from midway bends 320b. The position of strut 321a and 321b are fixed relative to each other so that the strut 321a and 321b cannot rotate or turn forcing movement about the midway bends 320a and 320b. The left midway bend 320a and right midway bend 320b of each of the articulated wire loops 220 results in a tension that causes the self-expanding wire framework 200 to engage in a circumferential flaring motion and end out of plane when deployed from the deployment tube. Further deployment of the framework 200 allows the left and right midway bends 320a and 320b of each of the articulated wire loops 220 making up the framework 200 to straighten out in a configuration with higher elastic energy which reorients the top segment 300 back towards the center. The self-expanding wire framework 200 has partially overlapping articulated wire loops 220 which are covered by polymer film 221. Each articulated wire loop has a left midway bend 320a and a right midway bend 320b. The adjacent wire loop at least partially overlaps a second wire loop by placing the left midway bend of a first wire loop behind the right midway bend of the second wire loop this pattern is repeated until the desired number of the articulated wire loops are achieved.

To illustrate how the self-expanding wire framework 200 able to advance around a heart 2 from an apical approach, FIGS. 3a-3b depict an embodiment of the present invention at successive amounts of deployment about a plastic mock heart 2 (3D printed from a CT scan of a normal adult sheep).

FIGS. 3a-3e illustrated the flaring and straightening of the framework 200 as it was deployed from the deployment tube 400. However, the flaring motion can also be observed with just a single articulated wire loop as seen in FIGS. 4-8.

FIG. 3a shows the self-expanding wire framework 200 compressed inside deployment tube 400 as it is deployed about a plastic mock heart 2. FIG. 3a shows a polymer film 221 with an articulated wire loop 220 with the top segment 300 flanked by the left and right midway bends 320a and 320b and include strut 321a extending from midway bends 320a and strut 321b extending from midway bends 320b as it is deployed from the deployment tube 400. The articulated wire loop 220 is deployed from the deployment tube 400 such that the left and right midway bends 320a and 320b are within the deployment tube 400.

FIG. 3b shows the initial deployment of framework 200 wherein the top segments 300 of each of the articulated wire loop 220 are beginning to engage in a circumferential flaring motion and bend out of plane as it is deployed about a plastic mock heart 2. FIG. 3b shows a polymer film 221 with an articulated wire loop 220 with the top segment 300 flanked by the left and right midway bends 320a and 320b and include strut 321a extending from midway bends 320a and strut 321b extending from midway bends 320b as it is deployed from the deployment tube 400. The articulated wire loop 220 is deployed from the deployment tube 400 such that the left and right midway bends 320a and 320b are extending from the deployment tube 400.

FIG. 3c illustrates the framework deployed to the midway bends 320 which are bent outwards flaring the top segment 300 out. As the framework 200 is deployed pass the midway bends 320, about a plastic mock heart 2. FIG. 3c shows a polymer film 221 with an articulated wire loop 220 with the top segment 300 flanked by the left and right midway bends 320a and 320b and include strut 321a extending from midway bends 320a and strut 321b extending from midway bends 320b as it is deployed from the deployment tube 400. The articulated wire loop 220 is deployed from the deployment tube 400 such that the left and right midway bends 320a and 320b and the polymer film 221 are extending past the deployment tube 400.

FIG. 3d shows the struts 321a and 321b connected to midway bends 320a and 320b which straighten out to configure to a form of higher elastic energy. The framework 200 is deployed pass the midway bends 320, about a plastic mock heart 2. FIG. 3d shows a polymer film 221 with an articulated wire loop 220 with the top segment 300 flanked by the left and right midway bends 320a and 320b and include strut 321a extending from midway bends 320a and strut 321b extending from midway bends 320b as it is deployed from the deployment tube 400. The articulated wire loop 220 is deployed from the deployment tube 400 such that the left and right midway bends 320a and 320b are extending past the deployment tube 400. As the midway bends 320a and 320b are straightened out, the top segment 300 of each articulated wire loop 220 are reoriented inwards from the initial flared position. The reorientation of the articulated wire loops 220 allows the top segment 300 of each wire loop 220 and the polymer film 221 to make contact with the outer circumference of the heart 2.

FIG. 3e illustrates the full deployment of the framework 200 as each articulated wire loop 220 is further expanded to encircle a larger portion of the heart 2. The framework 200 is deployed pass the midway bends 320, about a plastic mock heart 2. FIG. 3e shows a polymer film 221 with an articulated wire loop 220 with the top segment 300 flanked by the left and right midway bends 320a and 320b and include strut 321a extending from midway bends 320a and strut 321b extending from midway bends 320b as it is deployed from the deployment tube 400. The articulated wire loop 220 is deployed from the deployment tube 400 such that the left and right midway bends 320a and 320b and the polymer film 221 are extending past the deployment tube 400 to encircle a larger portion of the heart 2.

The self-expanding wire framework device of the present invention includes multiple articulated wire loops with a polymer film connected thereto. The number of articulated wire loops used is at the discretion of the manufacturer and depends on the size of the deployable device. As little as 2 articulated wire loops can be used, but the number can increase to 3, 4, 5, 6, 7, 8, 9, 10, 11, 12, or more articulated wire loops linked. Each of the articulated wire loops include struts that connect the midway bends to the hub (not shown). The struts are fixed in position relative to the midway bends to induce flaring when extended from the deployment tube. The fixation location can vary with the deployment of the framework as tension between the articulate wire loops may move the linkage. However, the struts between the loops may also be fixated to limit the maximum expansion size of the wire framework.

Figure 4D:
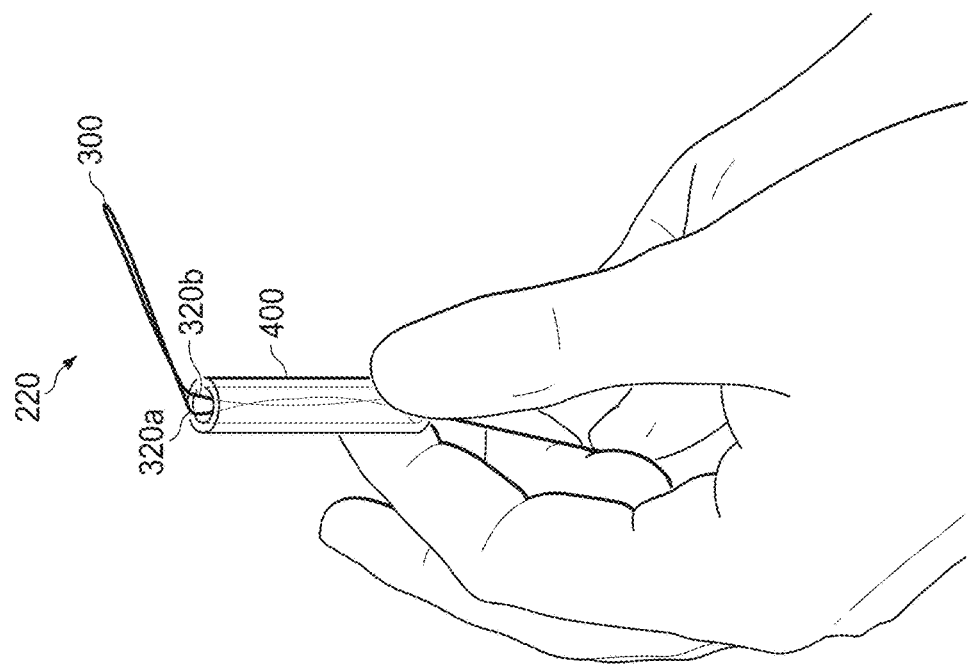
Figure 4C:
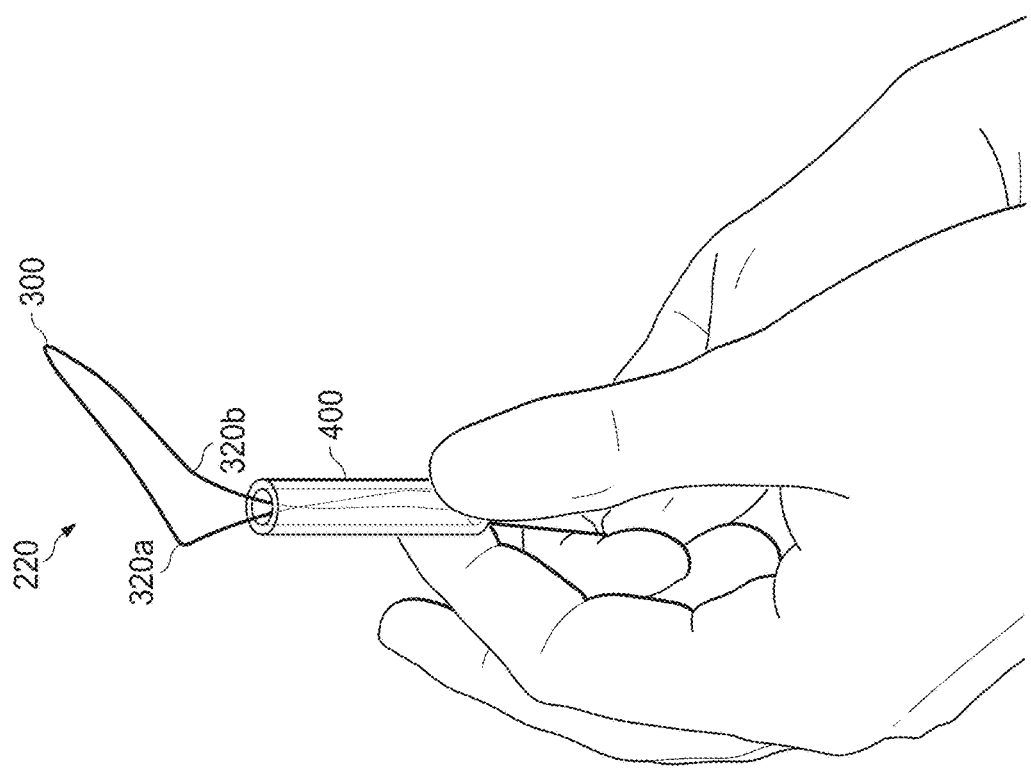

FIGS. 4a-4d depicts a side view of an embodiment of the present invention showing a single articulated wire loop 220 being drawn into the deployment tube 400. In FIG. 4a the articulated loop 220 is beginning to be drawn into the deployment tube 400 which compresses the left and right midway bends 320a and 320b together to allow top segments 300 to move inwardly. In FIG. 4b the articulated loop 220 is beginning to be drawn into the deployment tube 400 which compresses the left and right midway bends 320a and 320b together. At this point, flaring of the top segment 300 is evident between FIGS. 4a and 4b. Instead of the wire loop 220 collapsing in-plane and forced into the deployment tube 400, the left and right midway bends 320a and 320b each rotate to orient their top segments 300 out of plane. FIG. 4c shows an oriented wire loop 220 with the left and right midway bends 320a and 320b bent and flaring the top segment 300 outwardly. FIG. 4d shows the articulated wire loop 220 drawn into the deployment tube 400 to the left and right midway bends 320a and 320b. Each of the articulated wire loops 220 will have a pair of struts extending into the deployment tube 400 that may or may not be compressed. The present invention would still function if the loop ends were crossed or parallel within the deployment tube 400.

Figure 5B:
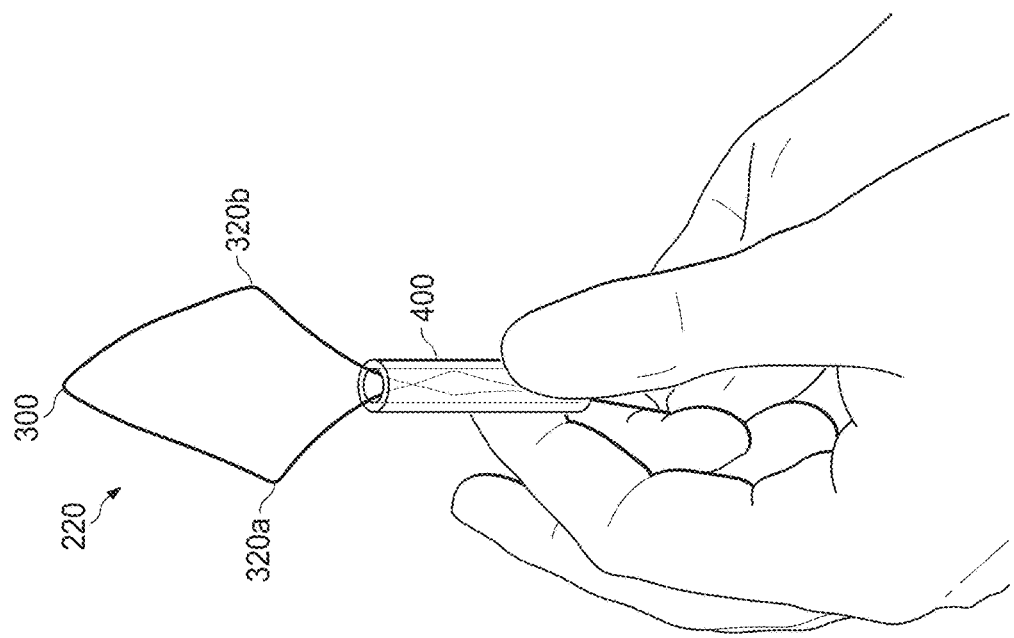
FIGS. 5a-5d depicts a frontal view of an embodiment of the present invention showing a single articulated wire loop being drawn into the deployment tube.
Figure 5A:
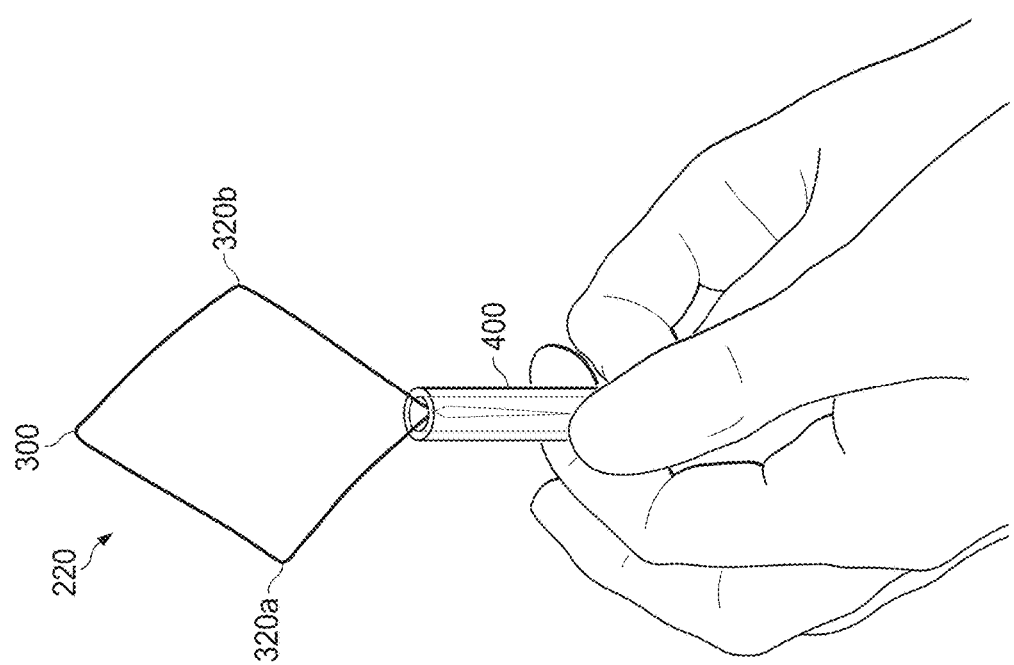
Figure 5D:
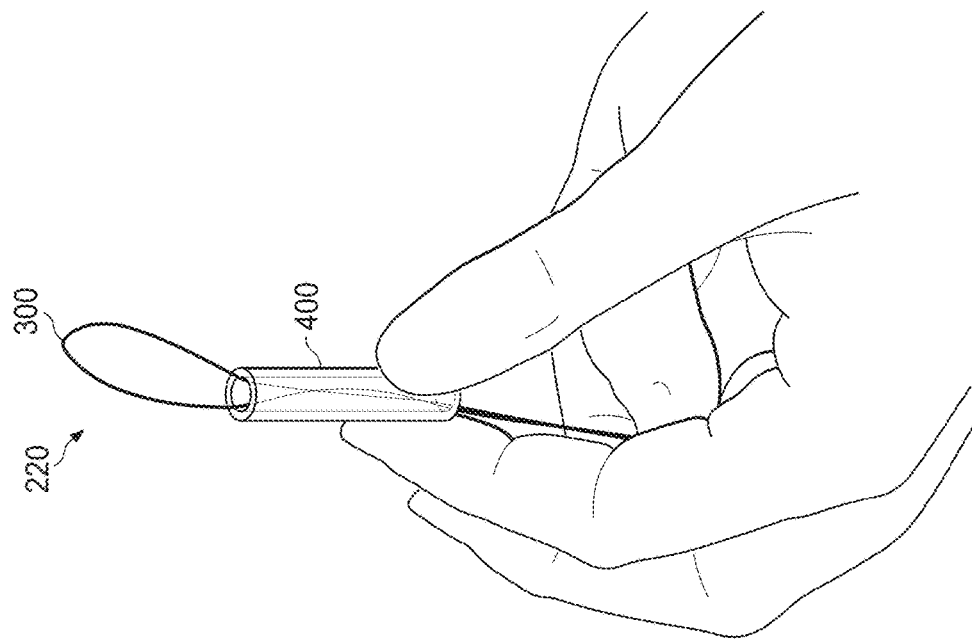
Figure 5C:
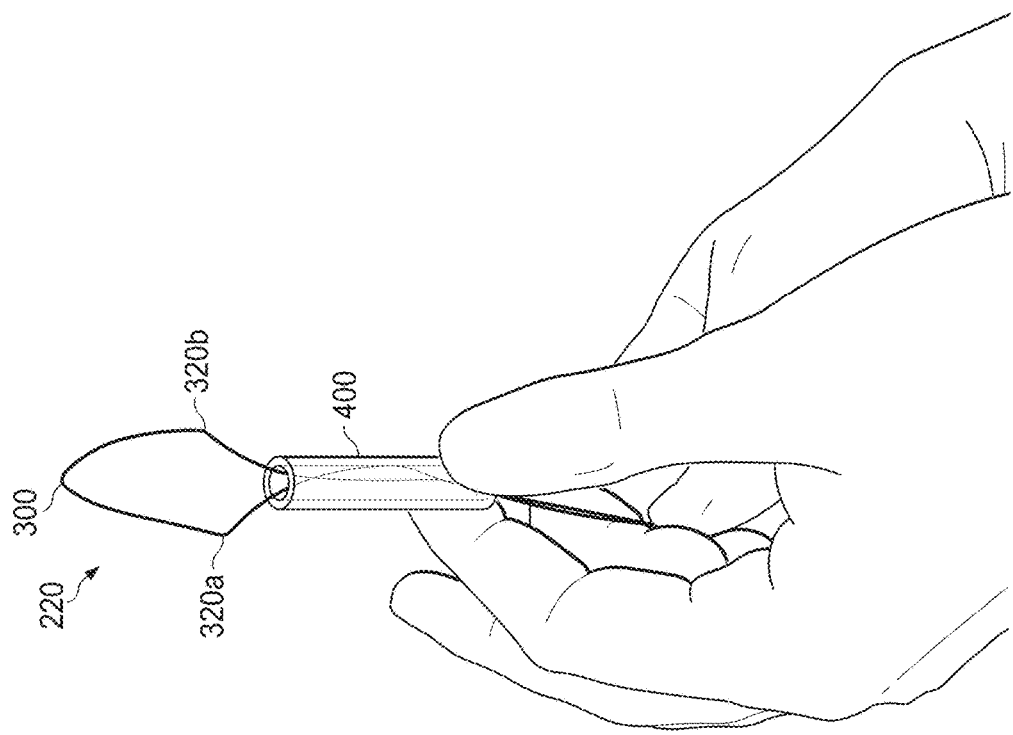

FIGS. 5a-5d depicts a frontal view of the single articulated wire loop 220 being drawn into the deployment tube 400 and correspond with FIGS. 4a-4d respectively. The bending and flaring of the midway bends 320a and 320b in the deployment tube 400 cannot be seen in the frontal view, but the compression of the midway bends 320a and 320b together is clear. FIGS. 5b and 5c show the reorientation of the wire loop 220 as the midway bends 320a and 320b are compressed into the deployment tube 400. FIG. 5d shows that after the midway bends 320a and 320b are reached, the rest of the wire loop up to the top segment 300 are compressed together to be drawn into the deployment tube 400. However, this compressed form is the configuration the loop 220 will be deployed at which leads to the initial flaring out position shown in FIG. 4d when the wire loop 220 is first deployed.

As noted herein, there are a number of features and advantages of the apparatus and method of the present invention, including: the apparatus is adapted to permit deployment of a deployable device, such as a heart assist or cardiac compression device; the self-expanding wire framework equipped with the deployable device being collapsible to fit inside the deployment tube to be positioned near the heart, and then deployed to advance around a heart without the need of any guidewires; the apparatus comprising a minimal number of components—including a self-expanding wire framework adapted to engage a deployable device, expand the deployable device and guide the deployable device during deployment; and the self-expanding wire framework and deployment tube being separated or integrated into a single unit.

Once the self-expanding wire framework is deployed from the deployment, controlled expansion and outward bend of the framework can aid in the positioning and implantation of the deployable device. The wire used for constructing the self-expanding wire frame will need to be an appropriate wire stiffness to achieve desired expansion and flaring out but not cause inversion of the wireframe during deployment. The use of quadrilateral or non-round wires will allow orienting the wire cross section such that it naturally causes the flaring motion upon deployment from the deployment tube. An example would be a rectangular wire with the long length of the cross-section oriented along the periphery of the device, around the heart. Furthermore, when engaging the deployable device with the self-expanding wire framework, the self-expanding wire fragment should be in a flaring position with the top segment 300 of each of the articulated wire loops out of plane.

In other embodiment of the invention, the midway bends of the articulated wire loop can be made more rounded to allow for gradual flaring as the framework is deployed. In another embodiment, the midway bends can also comprise multiple bends (two bends instead of one midway bend). Other embodiments can include 3, 4, 5 or more bends depending on the preference of the manufacturer. The diamond shape of the articulated wire loop is not the only possible element design. Various other shapes and designs are possible as long as there is a bending top segment 300 and midway bends in a left segment and a right segment that bend outward when the wire loop is collapsed and packed into the deployment tube.

Figure 6A:
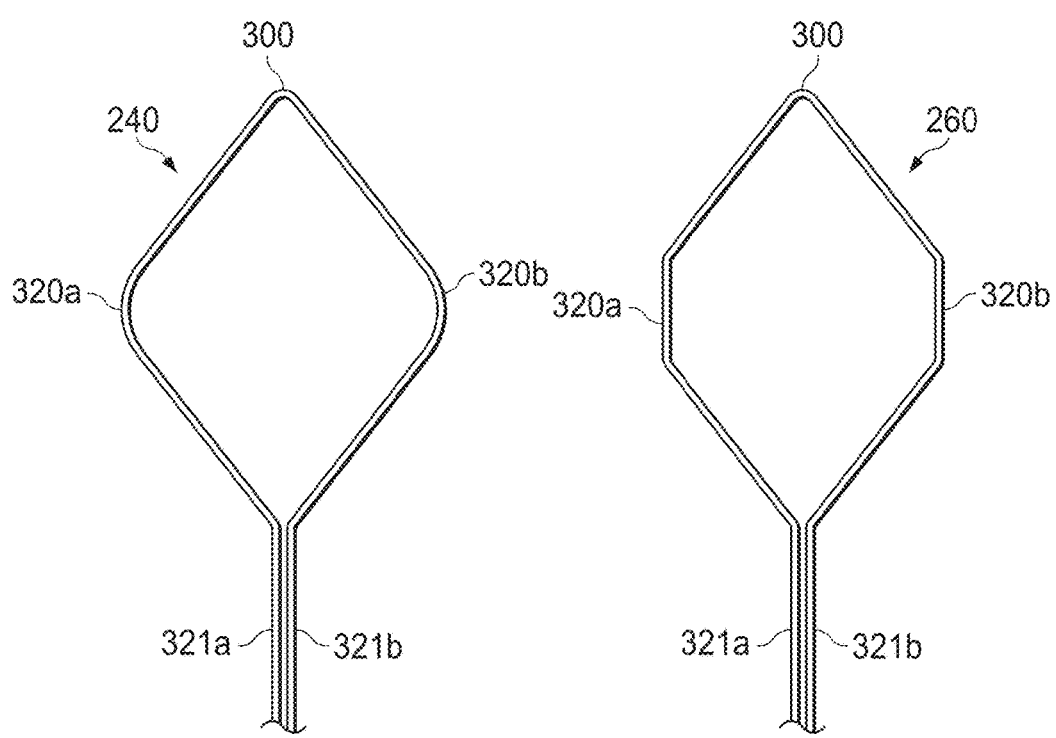
FIGS. 6a-6c depicts other embodiments of the present invention showing different designs of midway bends in the articulate wire loop.

FIG. 6a shows a schematic of an embodiment of articulated wire loop 240 with the top segment 300 flanked by the left and right midway bends 320a and 320b which are more rounded and include strut 321a extending from midway bends 320a and strut 321b extending from midway bends 320b into the deployment tube (not shown). Another embodiment includes articulated wire loop 260 with the top segment 300 flanked by the left and right midway bends 320a and 320b which are more flat and include strut 321a extending from midway bends 320a and strut 321b extending from midway bends 320b into the deployment tube (not shown).

Figure 6C:
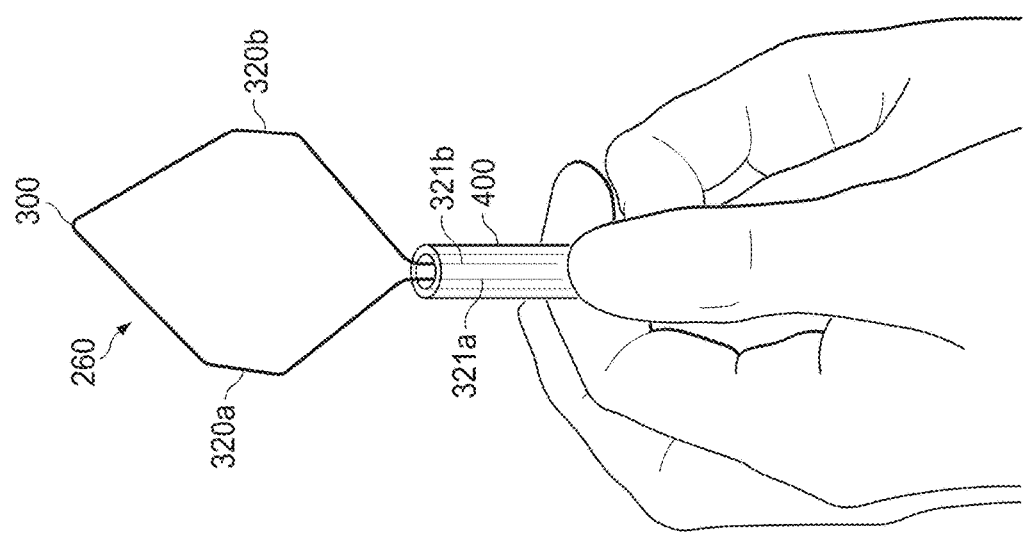
Figure 6B:
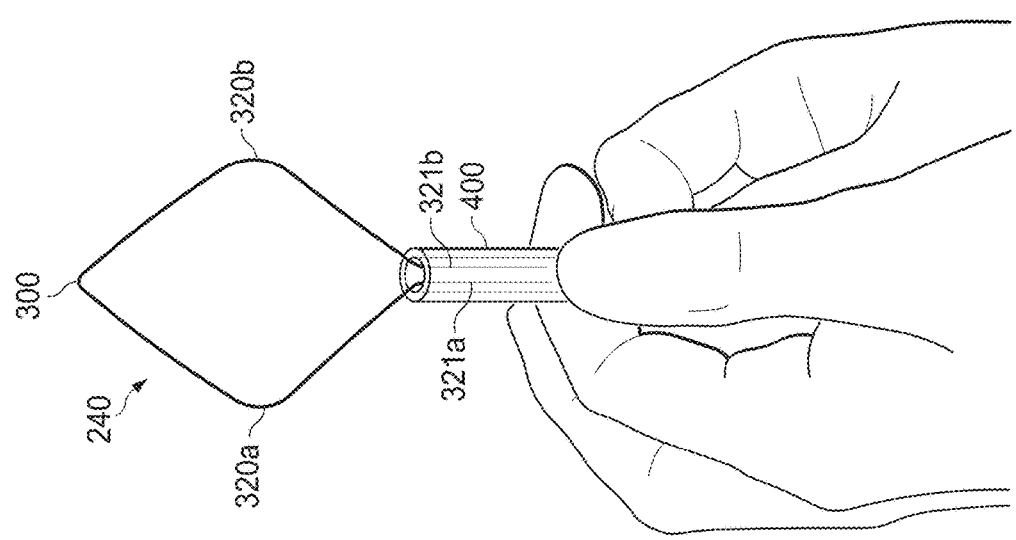

FIG. 6b shows an articulated wire loop 240 with the top segment 300 flanked by the left and right midway bends 320a and 320b which are more rounded and include strut 321a extending from midway bends 320a and strut 321b extending from midway bends 320b into the deployment tube 400.

FIG. 6c shows an articulated wire loop 260 with the top segment 300 flanked by the left and right midway bends 320a and 320b which are more flat and include strut 321a extending from midway bends 320a and strut 321b extending from midway bends 320b into the deployment tube 400.

FIGS. 7a-7d illustrate a side view of articulated wire loop 240 being drawn into deployment tube 400.

Figure 7B:
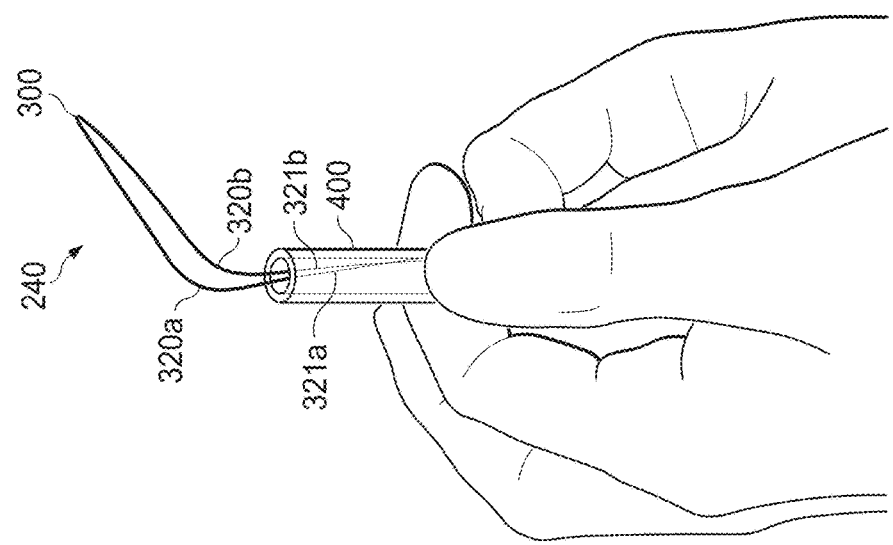
FIGS. 7a-7d depicts a side view of an embodiment of the present invention showing a single articulated wire loop with rounded midway bends being drawn into the deployment tube.
Figure 7A:
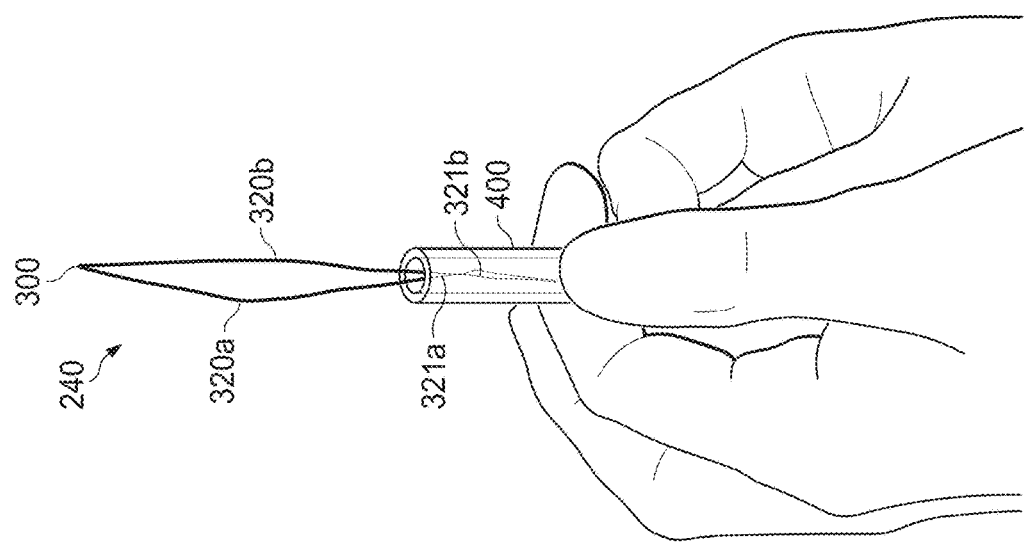

FIG. 7a shows an articulated wire loop 240 with the top segment 300 flanked by the left and right midway bends 320a and 320b which are more rounded and include strut 321a extending from midway bends 320a and strut 321b extending from midway bends 320b drawn into the deployment tube 400.

FIG. 7b shows an articulated wire loop 240 with the top segment 300 flanked by the left and right midway bends 320a and 320b which are more rounded and include strut 321a extending from midway bends 320a and strut 321b extending from midway bends 320b drawn into the deployment tube 400.

Figure 7D:
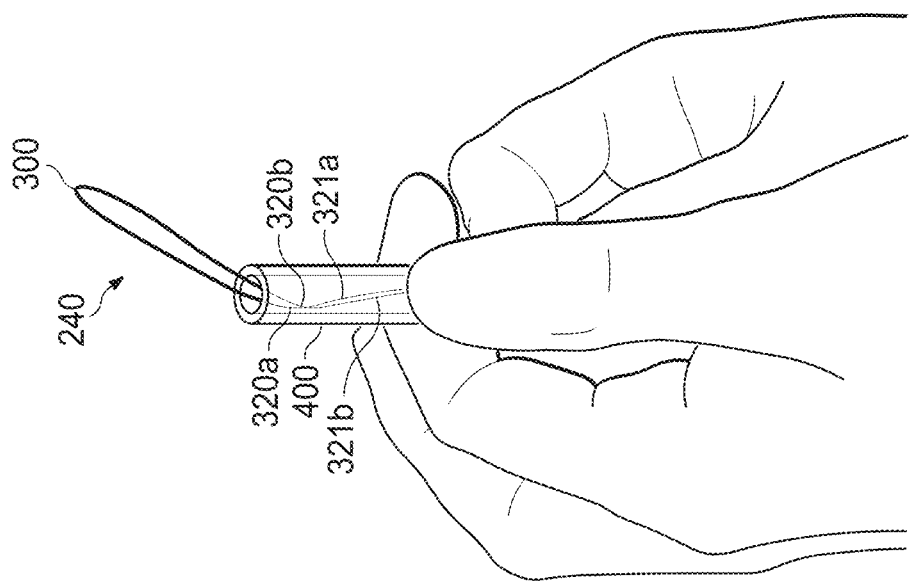
Figure 7C:
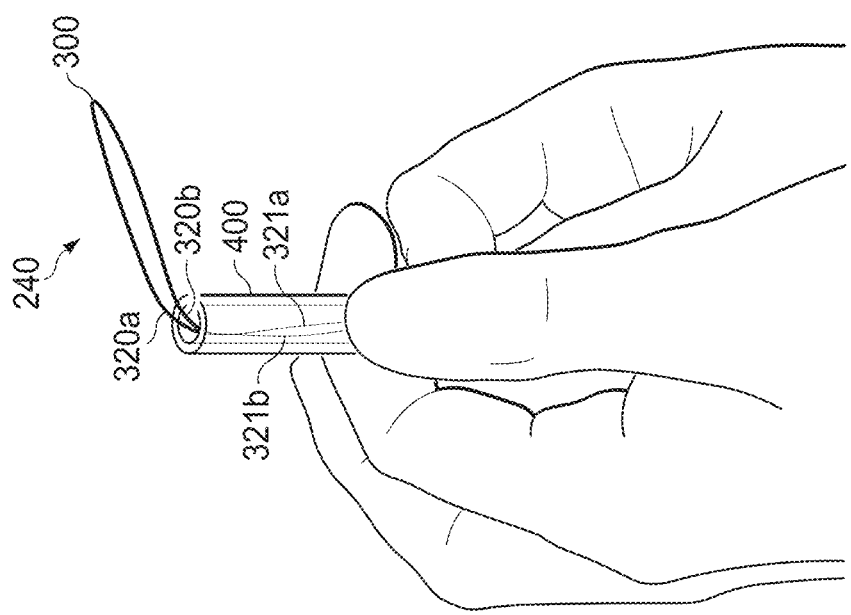

FIG. 7c shows an articulated wire loop 240 with the top segment 300 flanked by the left and right midway bends 320a and 320b which are more rounded and include strut 321a extending from midway bends 320a and strut 321b extending from midway bends 320b drawn into the deployment tube 400. The articulated wire loop 240 is drawn into the deployment tube 400 to the left and right midway bends 320a and 320b.

FIG. 7d shows an articulated wire loop 240 with the top segment 300 flanked by the left and right midway bends 320a and 320b which are more rounded and include strut 321a extending from midway bends 320a and strut 321b extending from midway bends 320b drawn into the deployment tube 400. The articulated wire loop 240 is drawn into the deployment tube 400 such that the left and right midway bends 320a and 320b are within the deployment tube 400.

Figure 8B:
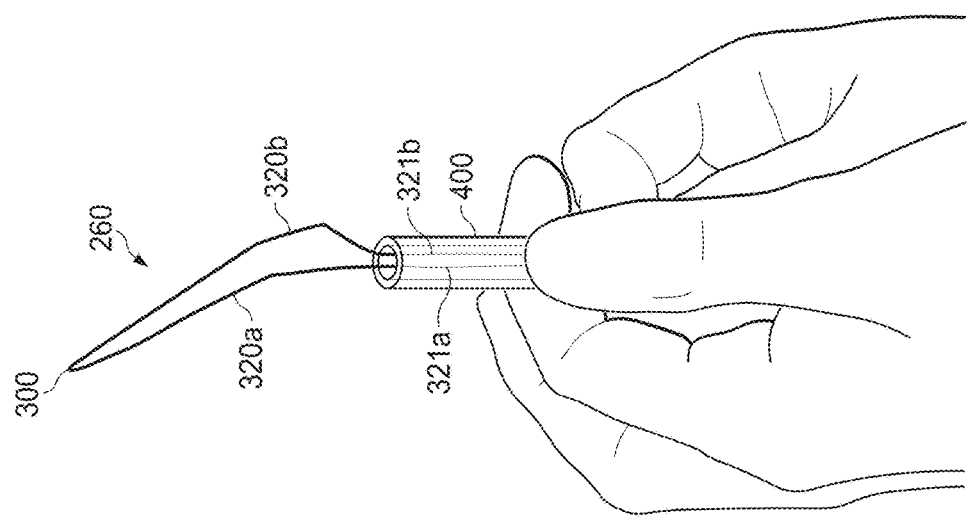
FIGS. 8*a*-8*d* depicts a side view of an embodiment of the present invention showing a single articulated wire loop with dual midway bends being drawn into the deployment tube.
Figure 8A:
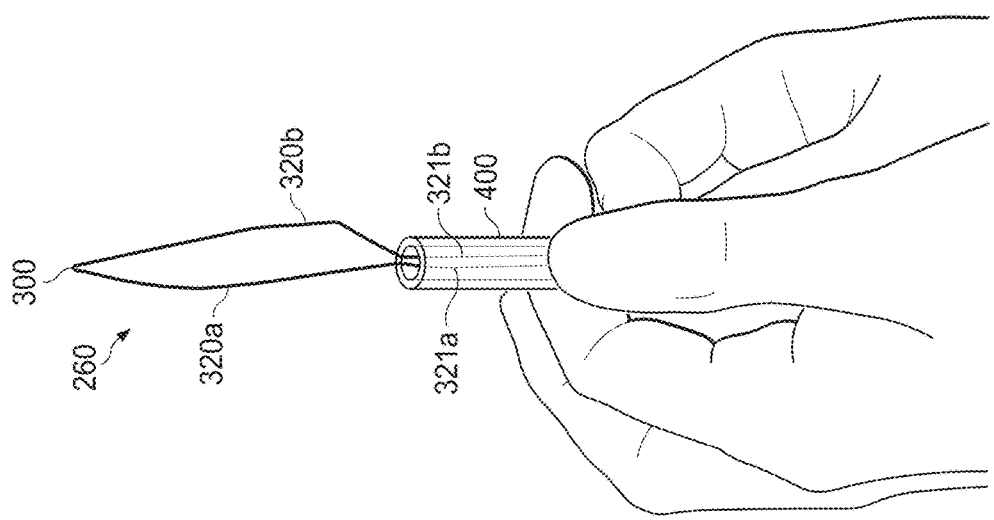

FIG. 8a shows an articulated wire loop 260 with the top segment 300 flanked by the left and right midway bends 320a and 320b which are more rounded and include strut 321a extending from midway bends 320a and strut 321b extending from midway bends 320b drawn into the deployment tube 400.

FIG. 8b shows an articulated wire loop 260 with the top segment 300 flanked by the left and right midway bends 320a and 320b which are more rounded and include strut 321a extending from midway bends 320a and strut 321b extending from midway bends 320b drawn into the deployment tube 400.

Figure 8D:
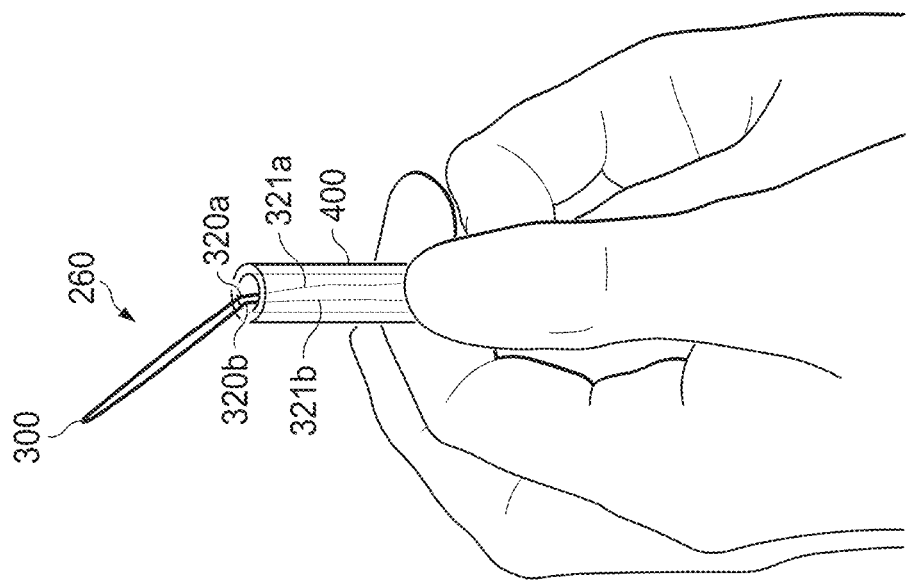
Figure 8C:
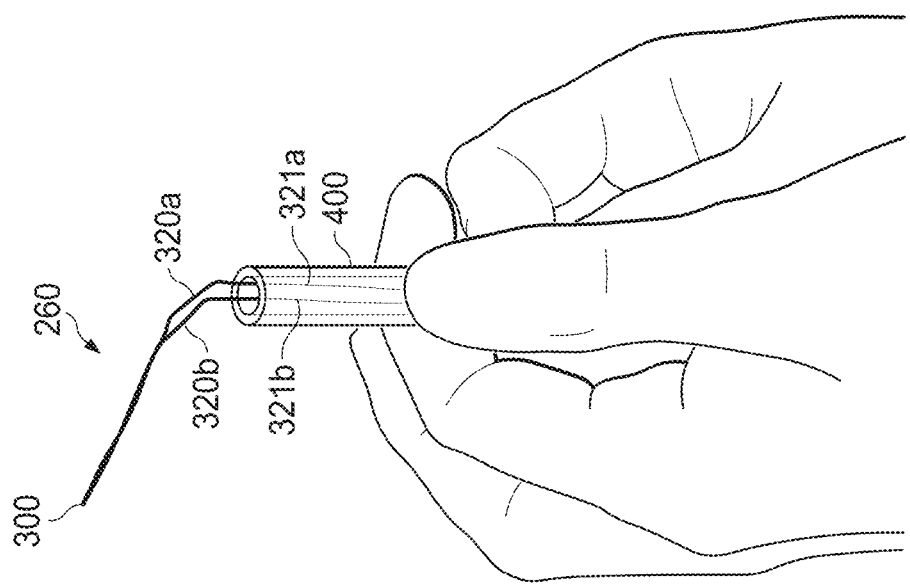

FIG. 8c shows an articulated wire loop 260 with the top segment 300 flanked by the left and right midway bends 320a and 320b which are more rounded and include strut 321a extending from midway bends 320a and strut 321b extending from midway bends 320b drawn into the deployment tube 400. The articulated wire loop 240 is drawn into the deployment tube 400 to the left and right midway bends 320a and 320b.

FIG. 8d shows an articulated wire loop 260 with the top segment 300 flanked by the left and right midway bends 320a and 320b which are more rounded and include strut 321a extending from midway bends 320a and strut 321b extending from midway bends 320b drawn into the deployment tube 400. The articulated wire loop 240 is drawn into the deployment tube 400 such that the left and right midway bends 320a and 320b are within the deployment tube 400.

Figure 9:
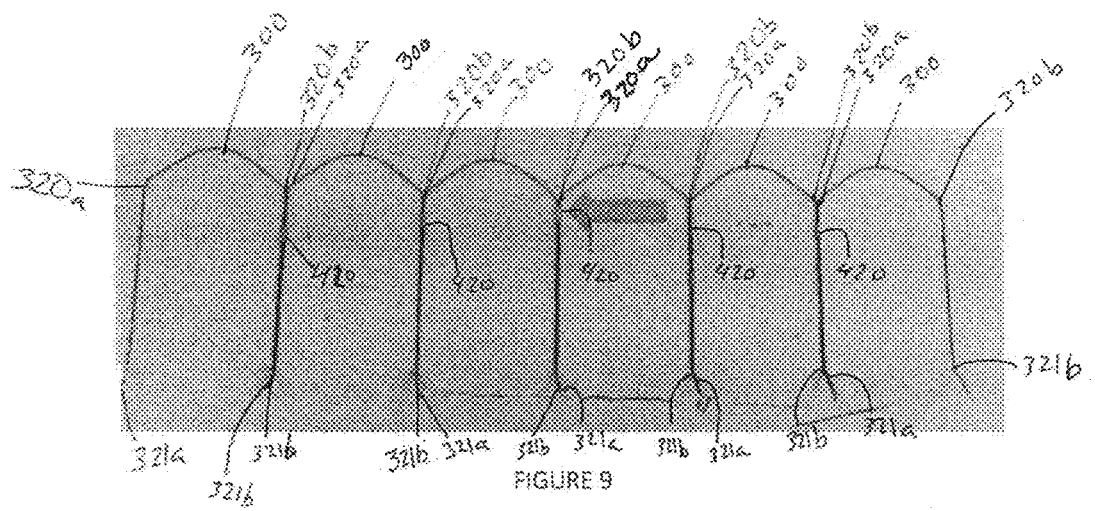
FIG. 9 is an image of a set of adjacent articulated wire loops.

FIG. 9 is an image of a set of adjacent articulated wire loops. FIG. 9 shows an articulated wire loop 260 with the top segment 300 flanked by the left and right midway bends 320a and 320b which are more rounded and include strut 321a extending from midway bends 320a and strut 321b extending from midway bends 320b with a crimp connector 420 connecting struts 321a and 321b from adjacent loops 300.

Figure 10:
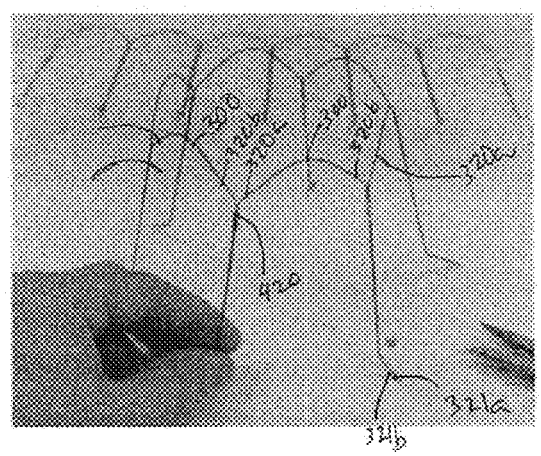
FIG. 10 is an image of the self-expanding wire framework.

FIG. 10 is an image of the self-expanding wire framework. FIG. 10 shows an articulated wire loop 260 with the top segment 300 flanked by the left and right midway bends 320a and 320b which are more rounded and include strut 321a extending from midway bends 320a and strut 321b extending from midway bends 320b with a crimp connector 420 connecting struts 321a and 321b from adjacent loops 300 to form a circular self-expanding wire framework.

Figure 11:
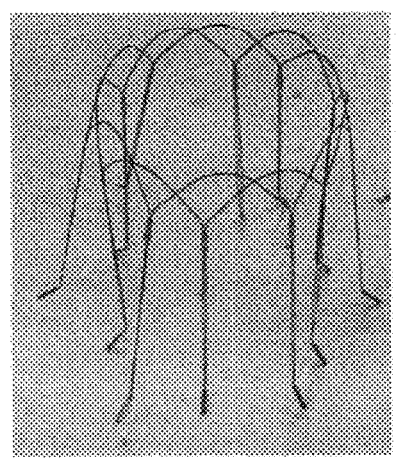
FIG. 11 is an image of a first set of adjacent articulated wire loops and a partially overlapping second set of adjacent articulated wire loops.

FIG. 11 is an image of a first set of adjacent articulated wire loops and a partially overlapping second set of adjacent articulated wire loops. FIG. 11 shows an articulated wire loop with the top segment flanked by the left and right midway bends and which are more rounded and include strut extending from midway bends and strut extending from midway bends with a crimp connector connecting struts and from adjacent loops.

Figures 12A, 12B:
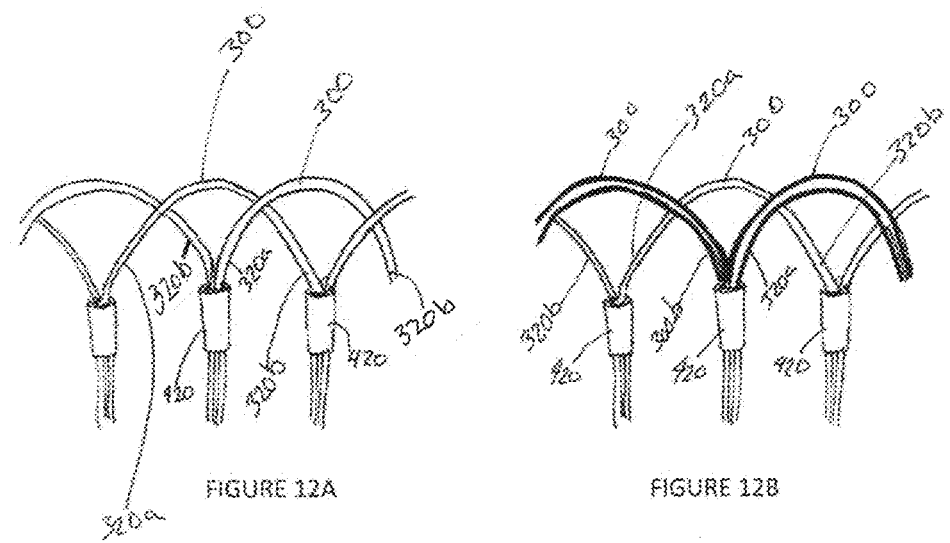
FIGS. 12A and 12B are an image of a first set of adjacent articulated wire loops and a partially overlapping second set of adjacent articulated wire loops showing the relationship between the loops.

FIGS. 12A and 12B are images of a first set of adjacent articulated wire loops and a partially overlapping second set of adjacent articulated wire loops showing the relationship between the loops. FIGS. 12A and 12B each show an articulated wire loop 260 with the top segment 300 flanked by the left and right midway bends 320a and 320b which are more rounded and include strut 321a extending from midway bends 320a and strut 321b extending from midway bends 320b with a crimp connector 420 connecting struts 321a and 321b from adjacent loops 300.

Figure 13:
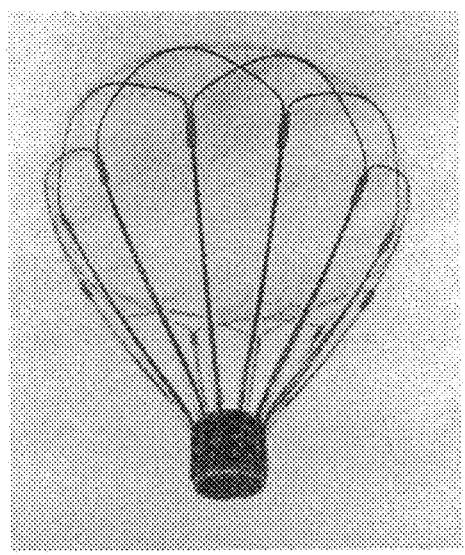
FIG. 13 is an image of one embodiment of the device of the present invention.

FIG. 13 is an image of one embodiment of the device of the present invention. FIG. 13 shows an articulated wire loop with the top segment flanked by the left and right midway bends and which are more rounded and include strut extending from midway bends and strut extending from midway bends with a crimp connector connecting struts and from adjacent loops.

Various attachment means may also be utilized between a polymer film chamber and the wire frame so as not to impede on desired bending. One example as shown in FIGS. 3a-3e is to strap the wires between layers of plastic. Another embodiment would be to allow wire movement and rotation within the polymer film attachment points.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. A self-expanding wire framework adapted to flare outwardly to encircle a portion of a heart comprising:
    a set of adjacent articulated wire loops extending from a hub, wherein each of the adjacent articulated wire loops of the set of adjacent articulated wire loops comprise:
        a top segment positioned at a lead edge and that extends to a left midway bend and to a right midway bend,
        a left strut that extends from the left midway bend to the hub, and
        a right strut that extends from the right midway bend to the hub;
    a connector that links the left strut to the right strut of each of the adjacent articulated wire loops;
    wherein the top segment, the left midway bend and the right midway bend result in a tension that causes each of the adjacent articulated wire loops to engage in a circumferential flaring motion and bend outwardly as the self-expanding framework is deployed.

2. The device of claim 1, wherein the connector is a crimp connector.

3. The device of claim 1, wherein the connector is a crimp connector, a wire connector, an adhesive, a weld, a clip or a combination thereof.

4. The device of claim 1, wherein the top segment, the left midway bend and the right midway bend form a triangular shape.

5. The device of claim 1, wherein the top segment, the left midway bend, the right midway bend the left strut and the right strut form a diamond shape.

6. The device of claim 1, further comprising a second self-expanding wire framework positioned in a staggered relationship to the first self-expanding wire framework.

7. The device of claim 1, wherein the left midway bends and the right midway bends are rounded to allow for gradual flaring as the self-expanding wire framework is deployed or wherein the left midway bends and the right midway bends are flattened to allow for flaring as the self-expanding wire framework is deployed.

8. The device of claim 1, wherein the left midway bends and the right midway bends further comprise multiple bends to allow for immediate flaring positions as the self-expanding wire framework is deployed.

9. The device of claim 1, where the self-expanding wire framework comprises at least 2, 3, 4, 5, 6, 7, 8, 9, 10, 11, 12, 13, 14, 15, 16, 17, 18, 19, 20 or more adjacent articulated wire loops.

10. The device of claim 1, further comprising a deployment tube to deploy the self-expanding wire framework, wherein the deployment tube comprises an outer surface surrounding an inner passage that restrains the self-expanding wire framework from the circumferential flaring motion and a deployment aperture to allow the self-expanding wire framework to flare outwardly as it exits the deployment tube.

11. The device of claim 1, further comprising a polymer film in contact with the self-expanding wire framework for deployment, wherein the polymer film is on the inside of the self-expanding wire framework, on the outside of the self-expanding wire framework or on the inside and the outside to sandwich the self-expanding wire framework.

12. A method for implanting a self-expanding framework delivery device about a heart, comprising the steps of:
    providing a self-expanding framework delivery device comprising a deployment tube having an outer surface surrounding an inner passage and a deployment aperture at one end of the inner passage;
    providing a self-expanding wire framework adapted to flare outwardly to encircle a portion of a heart comprising a set of adjacent articulated wire loops extending from a hub, wherein each of the adjacent articulated wire loops of the set of adjacent articulated wire loops comprise: a top segment positioned at a lead edge and that extends to a left midway bend and to a right midway bend, a left strut that extends from the left midway bend to the hub, and a right strut that extends from the right midway bend to the hub; a connector that links the left strut to the right strut of each of the adjacent articulated wire loops; wherein the top segment, the left midway bend and the right midway bend result in a tension that causes each of the adjacent articulated wire loops to engage in a circumferential flaring motion and bend outwardly as the self-expanding framework is deployed;

inserting the deployment tube into the thoracic cavity;

deploying the self-expanding wire framework from the deployment aperture;

moving the left midway bend and a right midway bend from the deployment aperture to allow a circumferential flaring motion and bend outwardly as the self-expanding framework is deployed; and extending the self-expanding wire framework from the deployment aperture to encircle at least a portion of the heart.

13. The method of claim 12, wherein the connector is a crimp connector.

14. The method of claim 12, wherein the connector is a crimp connector, a wire connector, an adhesive, a weld, a clip or a combination thereof.

15. The method of claim 12, wherein the top segment, the left midway bend and the right midway bend form a triangular shape.

16. The method of claim 12, wherein the top segment, the left midway bend, the right midway bend the left strut and the right strut form a diamond shape.

17. The method of claim 12, further comprising a second self-expanding wire framework positioned in a staggered relationship to the first self-expanding wire framework.

* * * * *